United States Patent
Luzi et al.

(10) Patent No.: US 8,609,161 B2
(45) Date of Patent: Dec. 17, 2013

(54) CONGLUTIN-GAMMA AS MEDICAMENT AND DIET SUPPLEMENT

(75) Inventors: Livio Luzi, Milan (IT); Ileana Marina Terruzzi, Milan (IT)

(73) Assignee: Ospedale San Raffaele S.R.L., Milan (IT)

( * ) Notice: Subject to any disclaimer, the term of this patent is extended or adjusted under 35 U.S.C. 154(b) by 121 days.

(21) Appl. No.: 12/994,959

(22) PCT Filed: May 28, 2009

(86) PCT No.: PCT/EP2009/056547
§ 371 (c)(1),
(2), (4) Date: Jan. 28, 2011

(87) PCT Pub. No.: WO2009/144278
PCT Pub. Date: Dec. 3, 2009

(65) Prior Publication Data
US 2011/0117226 A1    May 19, 2011

Related U.S. Application Data

(60) Provisional application No. 61/057,235, filed on May 30, 2008.

(51) Int. Cl.
*A61K 36/48* (2006.01)
(52) U.S. Cl.
USPC .......................... 424/757; 424/776; 514/12.1
(58) Field of Classification Search
None
See application file for complete search history.

(56) References Cited

FOREIGN PATENT DOCUMENTS

| DE | 20301675 U1 * | 5/2003 |
| WO | WO 01/19194 A1 * | 3/2001 |
| WO | 2004/071521 A1 | 8/2004 |
| WO | 2006/003110 A1 | 1/2006 |

OTHER PUBLICATIONS

Sironi (Eur Food Res Technol (2005), vol. 221, pp. 145-150).*
Sironi, et al., "A simple procedure of lupin seed protein fractionation for selective food applications", European Food Research and Technology, Zeitschrift for Lebensmitteluntersuchung, Und—Forschung A, Springer, Berlin, DE, vol. 221, No. 1-2, Jul. 1, 2005, pp. 145-150.
Waesche, et al., "New processing of lupin protein isolates and functional properties", Nahrung—Food, VCH Verlagsgesellschaft, Weinheim, XX, vol. 45, No. 6, Oct. 1, 2001, pp. 393-395.
Duranti, et al., "Grain legume proteins and nutraceutical properties", Fitoterapia, IDB Holding, Milan, IT, vol. 77, No. 2, Feb. 1, 2006, pp. 67-82.
Magni, et al., "Conglutin gamma, a lupin seed protein, binds insulin in vitro and reduces plasma glucose levels of hyperglycemic rats", Journal of Nutritional Biochemistry, Butterworth Publishers, Stoneham, GB, vol. 15, No. 11, Nov. 1, 2004, pp. 646-650.
Sirtori, et al., "Proteins of white lupin seed, a naturally isoflavone-poor legume, reduce cholesterolemia in rats and increase LDL receptor activity in HepG2 cells", Journal of Nutrition, Wistar Institute of Anatomy and Biology, Philadelphia, PA, US, vol. 134, No. 1, Jan. 1, 2004, pp. 18-23.

* cited by examiner

*Primary Examiner* — Susan Hoffman
(74) *Attorney, Agent, or Firm* — Lucas & Mercanti, LLP

(57) ABSTRACT

An enriched conglutin-γ protein extract from lupin seeds having a % by weight of conglutin-γ between 10 and 30%, or a conglutin-γ protein, or functional derivatives thereof for use as a medicament, as food integrator or diet supplement or integrator.

1 Claim, 17 Drawing Sheets

CONGLUTIN-GAMMA AS MEDICAMENT AND DIET SUPPLEMENT

CROSS-REFERENCE TO RELATED APPLICATIONS

This application is a 371 of PCT/EP2009/056547 filed May 28, 2009, which claims the benefit of U.S. Application No. 61/057,235 filed May 30, 2008, the contents of each of which are incorporated herein by reference.

FIELD OF INVENTION

The present invention relates to the effects of conglutin-γ on the IRS/AKT/P70S6k pathway as well as on MAP kinases, Cbl, caveolin 3 and GSK3 activation. It is shown that conglutin-γ regulates muscle energy metabolism, protein synthesis and MHC gene transcription through the modulation of the same components of the insulin signaling. Thus, conglutin-γ can be used orally in diabetes treatment and other insulin-resistant conditions as well as to improve muscle cells differentiation or muscle growth.

STATE OF THE ART

Lupin seed, an edible legume of the Mediterranean region, is referred to as an antidiabetic product by the traditional medicine. Conglutin-γ (accession: CAC16394), an abundant lupin seed glycoprotein, was found to be capable of binding mammalian insulin with a Kd of about $7\times10^{-5}$ M and caused a significant plasma glucose reduction when orally administered upon glucose overload trials in rats. For these reasons conglutin-γ was identified as the candidate molecule responsible for the claimed biological activity and the present invention examines its insulin-mimetic cellular mechanism of action. Insulin is the primary hormone responsible for proteosynthesis control, through IRS/AKT/P70S6k/PHAS1 pathways modulation, glucose homeostasis, achieved stimulating glucose transport, glucose uptake and glycogen synthesis through PKC, Flotilin 2, caveolin 3 and Cbl activation and muscle hypertrophy via muscle-specific MHC (myosin heavy chain) gene transcription control through ERKs insulin-mediated pathway.

Figure 1:
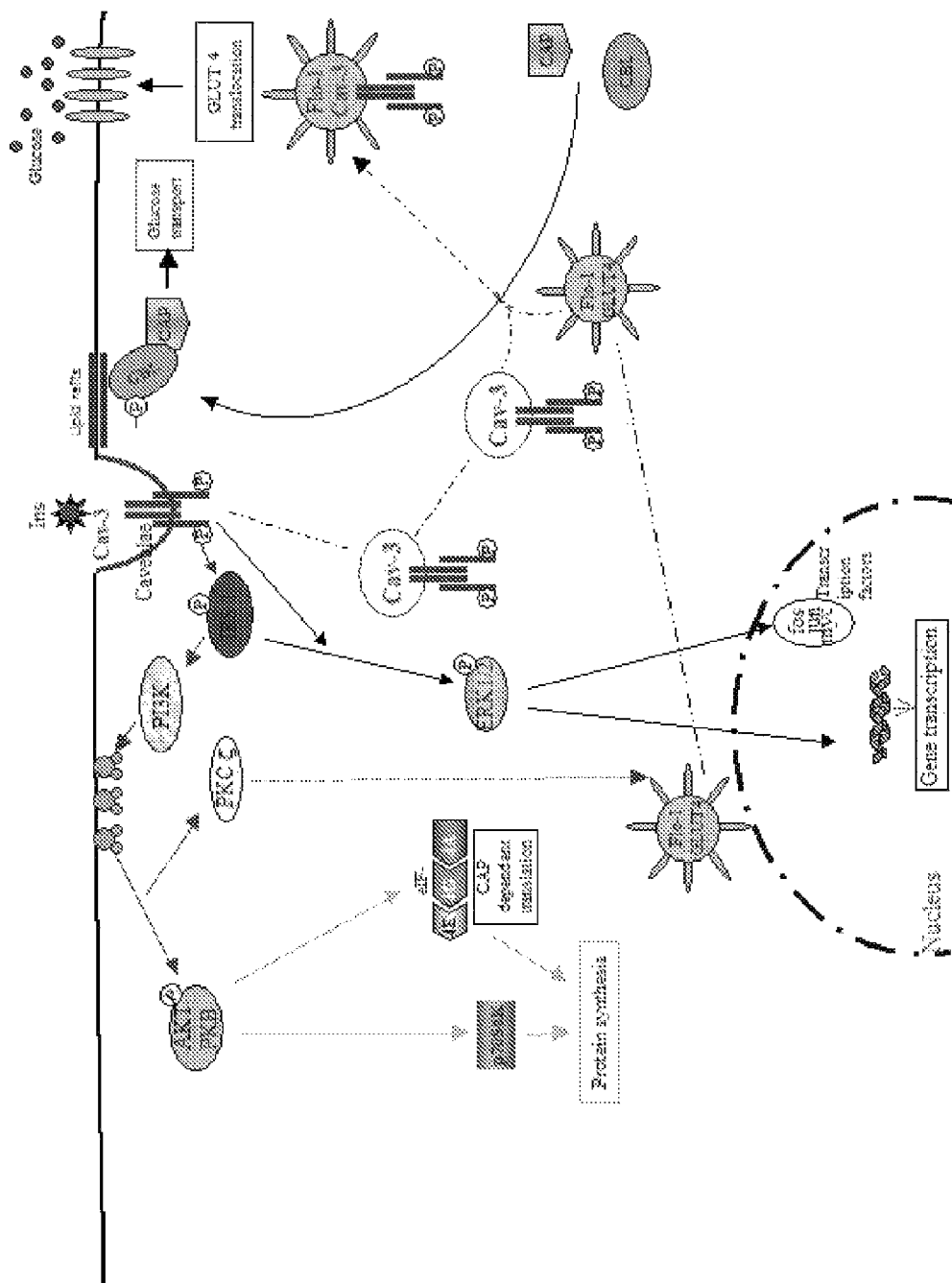

Lupin conglutin-γ is a mono-glycosylated protein which consists of two disulphide bonded subunits of 30 and 17 kDa. This monomeric unit undergoes pH-dependent reversible association to tetramer at neutral to slightly alkaline pH values (1, 2). Conglutin-γ in its native conformation is unusually resistant to proteolysis by trypsin (3) and other authors recently showed that conglutin-γ binds insulin in vitro with a Kd around $7\times10^{-5}$ M and significantly reduces plasma glucose in rodents in doses ranging from 30 to 120 mg/kg body weight (4). After insulin binds to its own receptor, it causes a series of phosphorylation/de-phosphorylation reactions which bring the insulin signal from the receptor to final metabolic and mitogenic pathways (FIG. 1).

The patent application WO2004071521 describes the use of lupin conglutin for the treatment of type II diabetes. In particular it discloses that pre-treatment of rats with lupin conglutin gamma significantly reduces the increase in glucose plasma levels induced by an oral administration of glucose 2 g/kg.

The patent application WO2005/077400 discloses a mixture of cysteine rich peptides for improving thiol homeostasis. In particular the peptides comprise at least 6.5% wt cystein and can be produced by cleaving the proteins of Lupin conglutin-γ into peptides that are then digested in peptides having a terminal cystein.

In the present invention the effect of conglutin-γ on an in vitro model of mouse myoblasts was evaluated, assessing the phosphorylation/activation of intracellular kinases common to the insulin signaling cascade. The results of the present invention surprisingly indicate that conglutin-γ shares with insulin common effects on the intracellular kinases tested herein, thus being an insulin-mimetic agent.

As a matter of facts, in the present invention it is surprisingly demonstrated that stimulation with both insulin and conglutin-γ resulted in persistent activation of kinases of the protein synthetic pathway as well as increase of glucose transport, GLUT4 translocation and ERKs dependent muscle-specific gene transcription regulation. These results indicate that conglutin-γ regulate muscle energy metabolism, protein synthesis and MHC gene transcription through the modulation of the same components of the insulin signaling. In particular, conglutin-γ modulates muscle cells differentiation and growth.

Besides, the present invention shows as conglutin-gamma promotes muscle anabolism assessing the lupin seed protein modulation of intracellular kinases involved in the insulin signalling cascade and insulin anabolic effect, in an in vivo mouse model.

Thus, this legume protein can be used as therapeutic agent in many pathologies as diabetes and other insulin-resistant conditions.

SUMMARY OF INVENTION

It is therefore an object of the present invention an enriched conglutin-γ protein extract from lupin seeds having a % by weight of conglutin-γ between 10 and 30%, or a conglutin-γ protein, or functional derivatives thereof for use as a medicament.

Another object is an enriched conglutin-γ protein extract from lupin seeds having a % by weight of conglutin-γ between 10 and 30%, or a conglutin-γ protein or functional derivatives thereof for use as food integrator or diet supplement or integrator.

Another object is an enriched conglutin-γ protein extract from lupin seeds having a % by weight of conglutin-γ between 10 and 30%, or a conglutin-γ protein, or functional derivatives thereof for use in the treatment of a metabolic syndrome.

Another object is an enriched conglutin-γ protein extract from lupin seeds having a % by weight of conglutin-γ between 10 and 30%, or a conglutin-γ protein, or functional derivatives thereof wherein the metabolic syndrome is characterized by resistance to insulin and/or obesity.

Another object is an enriched conglutin-γ protein extract from lupin seeds having a by weight of conglutin-γ between 10 and 30%, or a conglutin-γ protein, or functional derivatives thereof for use in the treatment of polycystic ovary syndrome.

Another object is an enriched conglutin-γ protein extract from lupin seeds having a % by weight of conglutin-γ between 10 and 30%, or a conglutin-γ protein, or functional derivatives thereof for use in the treatment of lipodystrophy.

Another object is an enriched conglutin-γ protein extract from lupin seeds having a % by weight of conglutin-γ between 10 and 30%, or a conglutin-γ protein, or functional derivatives thereof 6 wherein the lipodystrophy is caused by HIV.

Another object is an enriched conglutin-γ protein extract from lupin seeds having a by weight of conglutin-γ between 10 and 30%, or a conglutin-γ protein, or functional derivatives thereof for use in the treatment of a muscular dystrophy.

Another object is an enriched conglutin-γ protein extract from lupin seeds having a % by weight of conglutin-γ between 10 and 30%, or a conglutin-γ protein, or functional derivatives thereof for use to induce muscle cell differentiation and/or hypertrophy.

Another object is a method of treatment of a metabolic syndrome comprising administering to a subject in need thereof an effective amount of an enriched conglutin-γ protein extract from lupin seeds having a % by weight of conglutin-γ between 10 and 30%, or a conglutin-γ protein, or functional derivatives thereof. Preferably the metabolic syndrome is characterized by resistance to insulin and/or obesity.

Another object is a method of treatment of polycystic ovary syndrome comprising administering to a subject in need thereof an effective amount of an enriched conglutin-γ protein extract from lupin seeds having a % by weight of conglutin-γ between 10 and 30%, or a conglutin-γ protein, or functional derivatives thereof.

Another object is a method of treatment of lipodystrophy comprising administering to a subject in need thereof an effective amount of an enriched conglutin-γ protein extract from lupin seeds having a % by weight of conglutin-γ between 10 and 30%, or a conglutin-γ protein, or functional derivatives thereof. Preferably the lipodystrophy is caused by HIV.

Another object is a method of treatment of a muscular dystrophy comprising administering to a subject in need thereof an effective amount of an enriched conglutin-γ protein extract from lupin seeds having a % by weight of conglutin-γ between 10 and 30%, or a conglutin-γ protein, or functional derivatives thereof.

Another object is a method to induce muscle cell differentiation or muscle growth comprising the step of exposing said muscle cell or muscle to an effective amount of an enriched conglutin-γ protein extract from lupin seeds having a % by weight of conglutin-γ between 10 and 30%, or a conglutin-γ protein, or functional derivatives thereof.

Another object is a pharmaceutical composition comprising an effective amount of an enriched conglutin-γ protein extract from lupin seeds having a % by weight of conglutin-γ between 10 and 30%, or a conglutin-γ protein, or functional derivatives thereof, and proper additives and/or diluents. The composition may be for oral administration or any other suitable forms.

Another object is a diet integrator composition comprising an effective amount of an enriched conglutin-γ protein extract from lupin seeds having a % by weight of conglutin-γ between 10 and 30%, or a conglutin-γ protein, or functional derivatives thereof, and proper additives and/or diluents. The composition may be for oral administration or any other suitable forms.

The enriched conglutin-gamma protein extract by lupin seed (generally 10-30% by weight of total proteins) is prepared according to any method known to the skilled in the art, as according to ref. 25.

In the present invention a functional derivative of the conglutin-γ is represented, as a way of example by a protein fragment that retains the desired activity. In the present invention a metabolic syndrome is defined according to the American Diabetes Association Criteria (Expert Committee on the Diagnosis and Classification of Diabetes Mellitus, Report of the expert committee on the diagnosis and classification of diabetes mellitus, Diabetes Care 26 (2003) (Suppl. 1), pp. S5-S20).

DETAILED DESCRIPTION OF THE INVENTION

Figure Legends

The invention will be now described by non limiting examples referring to the following figures:

FIG. 1: Intracellular pathways of insulin signaling.

Figure 2:
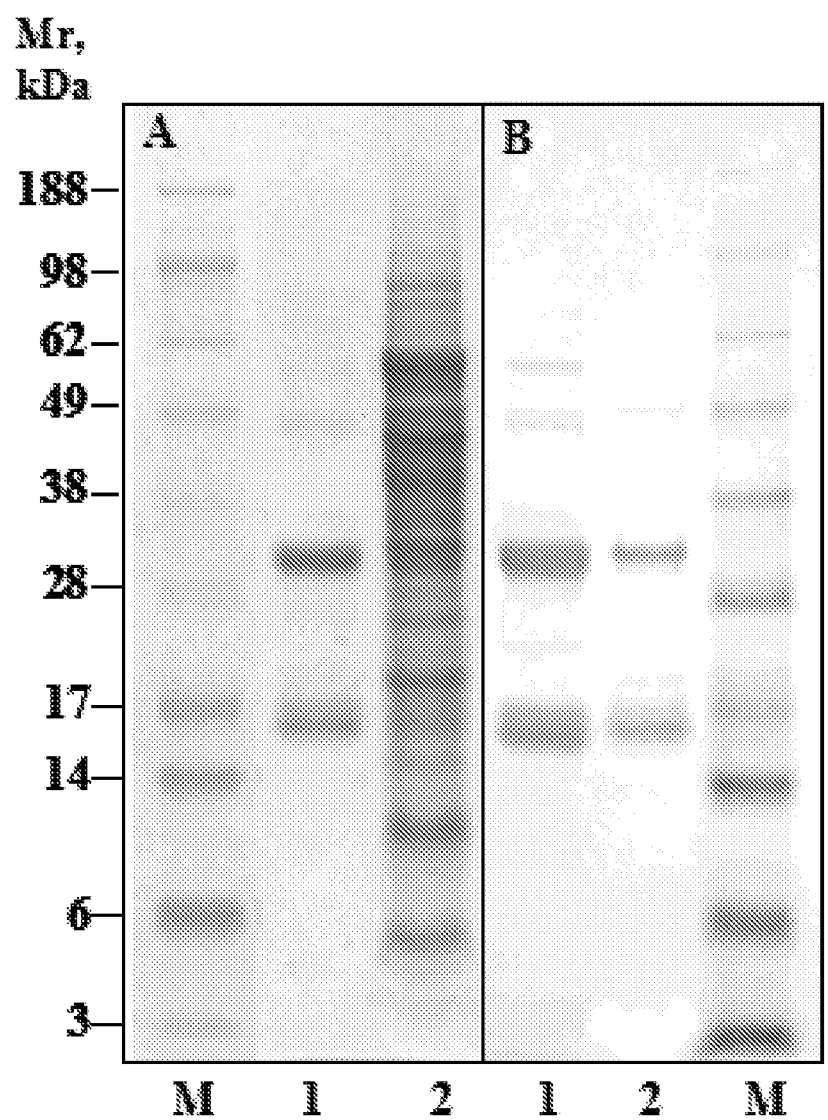

FIG. 2: Panel A: SDS-PAGE pattern under reducing conditions of the purified conglutin-γ (line: 1) as compared to the total lupin protein extract (line: 2). Two main bands of Mr around 30 and 16-17 kDa were visible. The sizes of these bands fitted with those of the large and small conglutin-γ subunits. A minor band of 48 kDa was previously found to correspond to uncleaved conglutin-γ precursor [unpublished results]. This protein preparation was judged sufficiently homogenous to be suitable for cell trials (M=markers). Panel B: the protein blot with specific antibodies confirmed the identity of the proteins and the lack of apparent differences between the purified conglutin-γ (line: 1) and the one in the total protein extract (line: 2) suggesting that no modification had occurred during the purification procedure. (M=markers).

Figure 3:
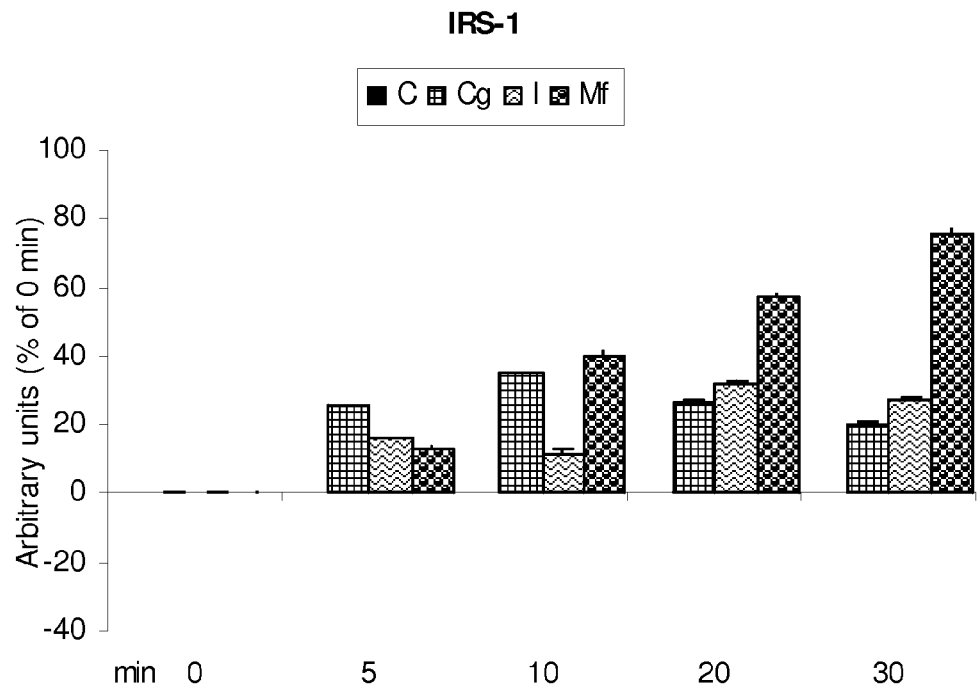

FIG. 3: Representative blot of insulin receptor substrate 1 protein content in C2C12 myofibers when not stimulated (C) or after insulin (I), conglutin-γ (Cg) or metformin (Mf) stimulation, at the times described in the Methods. The results of densitometry analyses are expressed as arbitrary units in relation to the amount of target protein at 0 min. Protein quantification was adjusted for the corresponding alpha-tubulin level.

Figure 4:
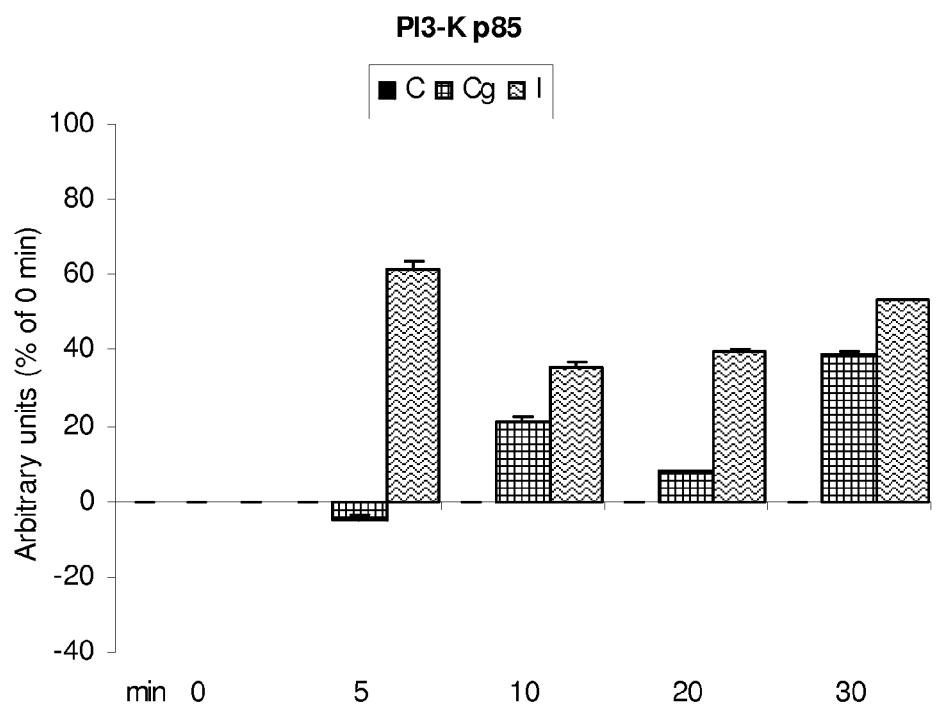

FIG. 4: Representative blot of the of PI3K-p85 subunit content in C2C12 myofibers when not stimulated (C) or after insulin (I) or conglutin-γ (Cg) stimulation at the times described in the Methods. The results of densitometry analyses are expressed as arbitrary units in relation to the amount of target protein at 0 min. Protein quantification was adjusted for the corresponding alpha-tubulin level.

Figure 5:
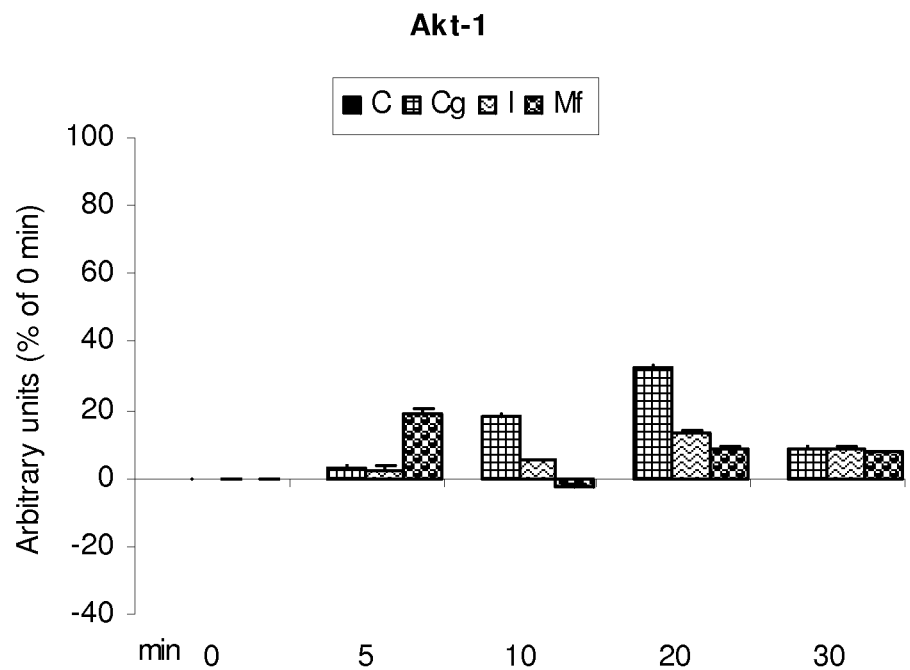

FIG. 5: Representative blot of AKT-1 protein content in C2C12 myofibers when not stimulated (C) or after insulin (I), conglutin-γ (Cg) or metformin (Mf) stimulation at the times described in the Methods. The results of densitometry analyses are expressed as arbitrary units in relation to the amount of target protein at 0 min. Protein quantification was adjusted for the corresponding alpha-tubulin level.

Figure 6:
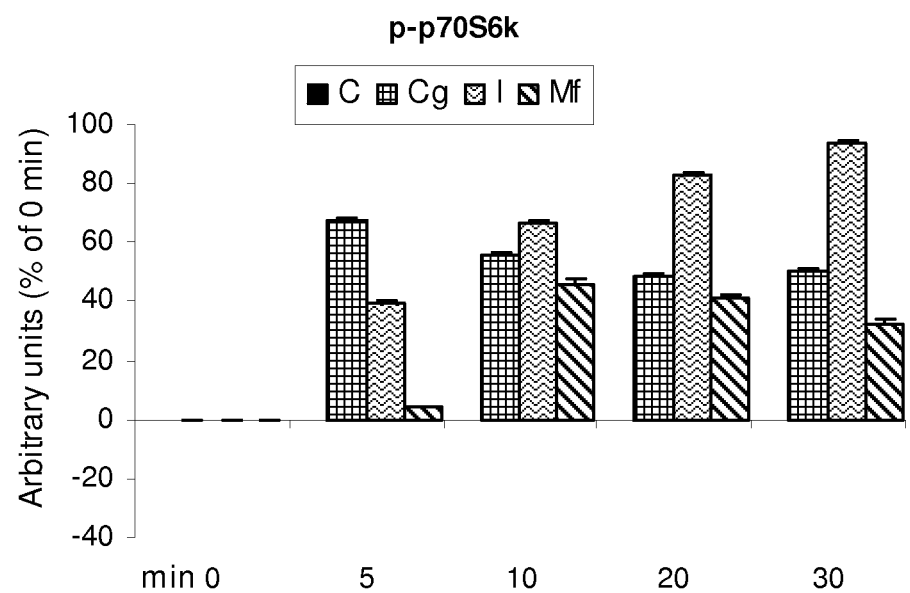

FIG. 6: Representative blot of p70S6K phosphorylation in C2C12 myofibers when not stimulated (C) or after insulin (I), conglutin-γ (Cg) or metformin (Mf) stimulation at the times described in the Methods. The results of densitometry analyses are expressed as arbitrary units in relation to the amount of target protein at 0 min. Protein quantification was adjusted for the corresponding alpha-tubulin level.

Figure 7:
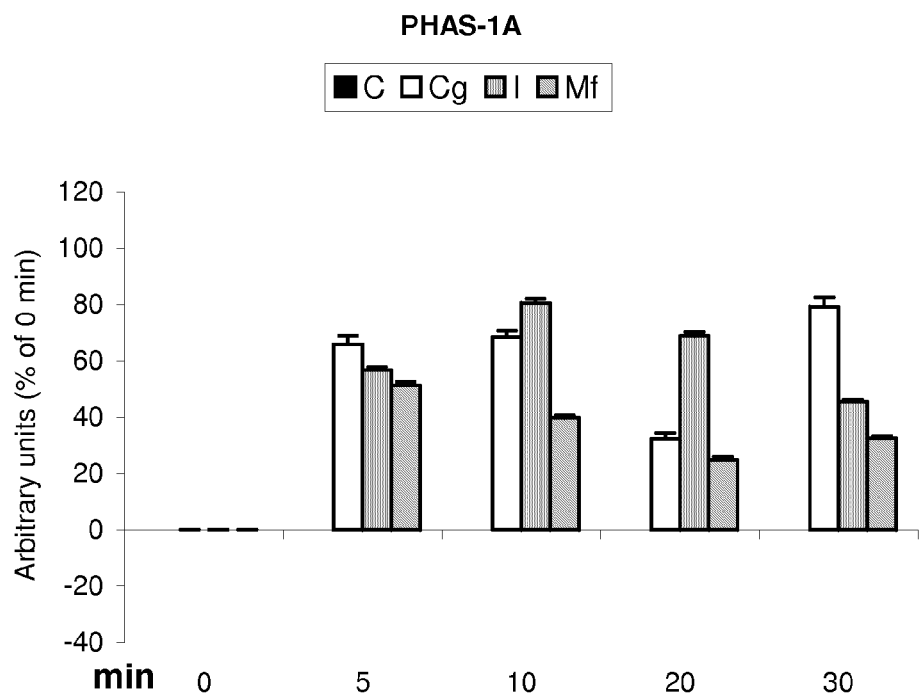

FIG. 7: Representative blot of PHAS-1α phosphorylation in C2C12 myofibers when not stimulated (C) or after insulin (I), conglutin-γ (Cg) or metformin (Mf) stimulation at the times described in the Methods. The results of densitometry analyses are expressed as arbitrary units in relation to the amount of target protein at 0 min. Protein quantification was adjusted for the corresponding alpha-tubulin level.

Figure 8:
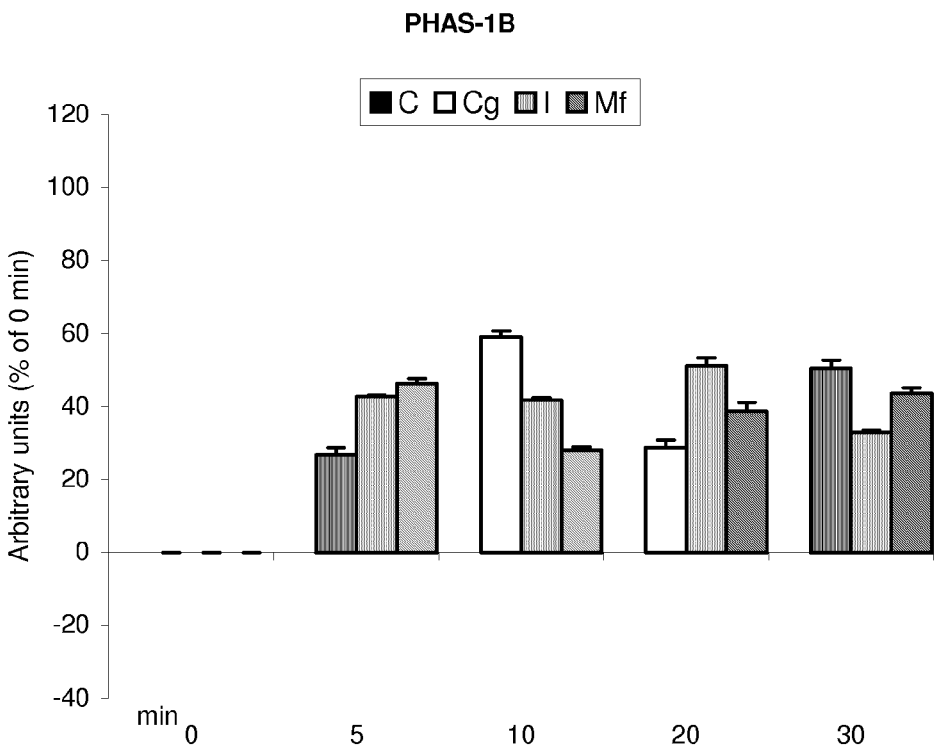

FIG. 8: Representative blot of PHAS-1 β phosphorylation in C2C12 myofibers when not stimulated (C) or after insulin (I), conglutin-γ (Cg) or metformin (Mf) stimulation at the times described in the Methods. The results of densitometry analyses are expressed as arbitrary units in relation to the amount of target protein at 0 min. Protein quantification was adjusted for the corresponding alpha-tubulin level.

Figure 9:
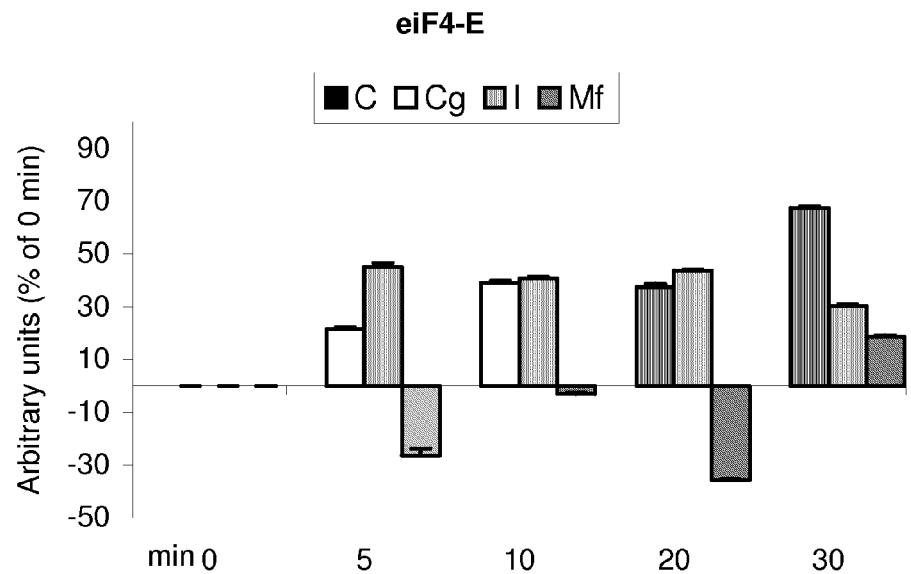

FIG. 9: Representative blot of eiF4-E protein content in C2C12 myofibers when not stimulated (C) or after insulin (I), conglutin-γ (Cg) or metformin (Mf) stimulation at the times described in the Methods. The results of densitometry analyses are expressed as arbitrary units in relation to the amount of target protein at 0 min. Protein quantification was adjusted for the corresponding alpha-tubulin level.

Figure 10:
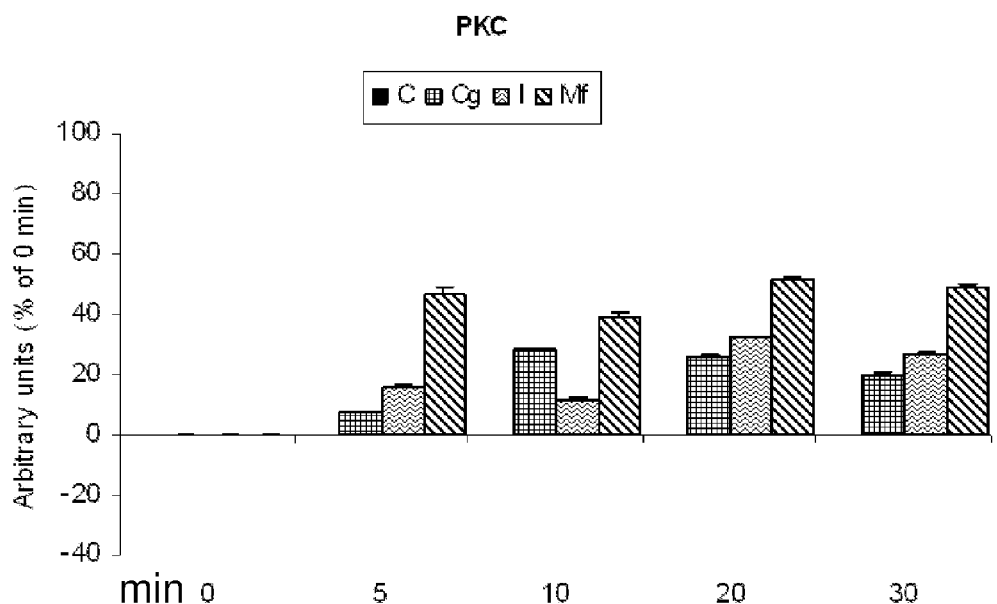

FIG. 10: Representative blot of PKC protein content in C2C12 myofibers when not stimulated (C) or after insulin (I), conglutin-γ (Cg) or metformin (Mf) stimulation at the times described in the Methods. The results of densitometry analyses are expressed as arbitrary units in relation to the amount of target protein at 0 min. Protein quantification was adjusted for the corresponding alpha-tubulin level.

Figure 11:
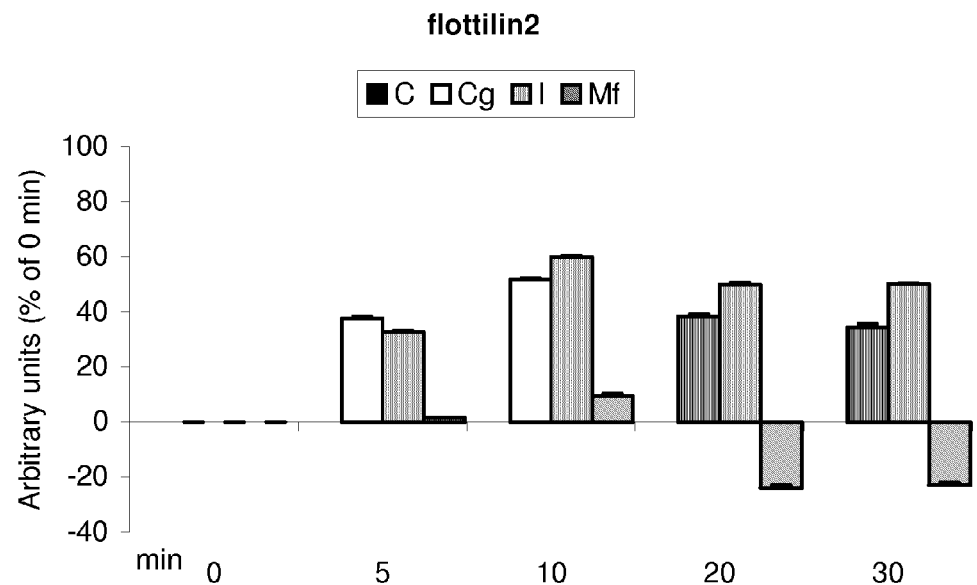

FIG. 11: Representative blot of flottilin-2 protein content in C2C12 myofibers when not stimulated (C) or after insulin (I), conglutin-γ (Cg) or metformin (Mf) stimulation at the times described in the Methods. The results of densitometry analyses are expressed as arbitrary units in relation to the amount of target protein at 0 min. Protein quantification was adjusted for the corresponding alpha-tubulin level.

Figure 12:
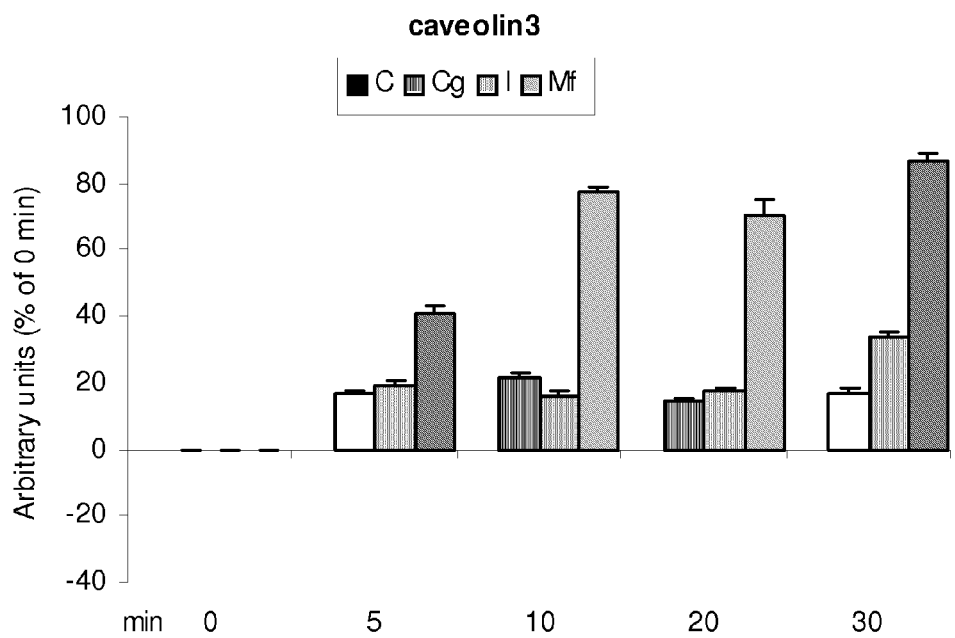

FIG. 12: Representative blot of caveolin-3 protein content in C2C12 myofibers when not stimulated (C) or after insulin (I), conglutin-γ (Cg) or metformin (Mf) stimulation at the times described in the Methods. The results of densitometry analyses are expressed as arbitrary units in relation to the amount of target protein at 0 min. Protein quantification was adjusted for the corresponding alpha-tubulin level.

Figure 13:
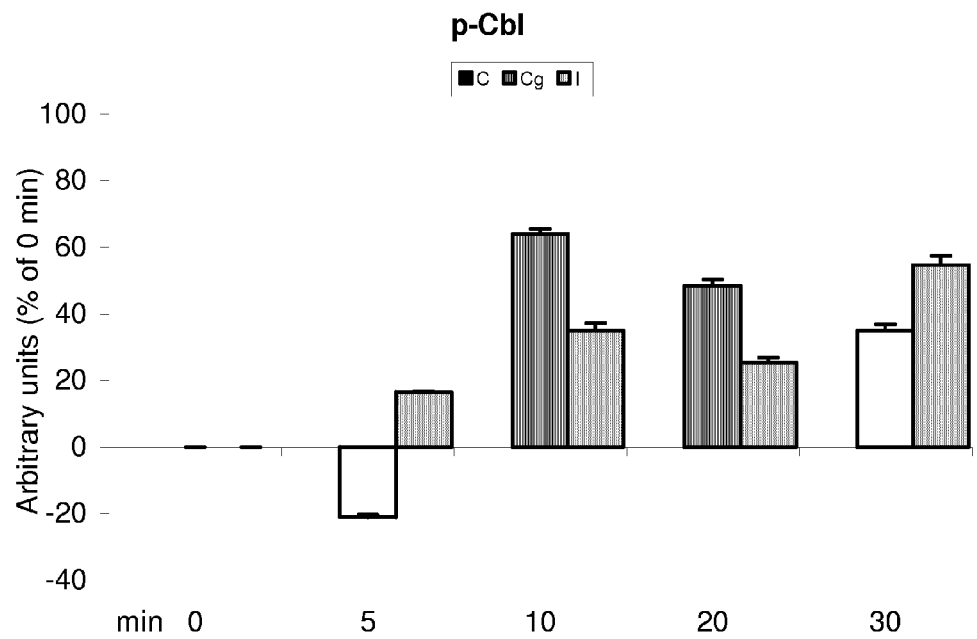

FIG. 13: Representative blot of Cbl phosphorylation in C2C12 myofibers when not stimulated (C) or after insulin (I) or conglutin-γ (Cg) stimulation at the times described in the Methods. The results of densitometry analyses are expressed as arbitrary units in relation to the amount of target protein at 0 min. Protein quantification was adjusted for the corresponding alpha-tubulin level.

Figure 14:
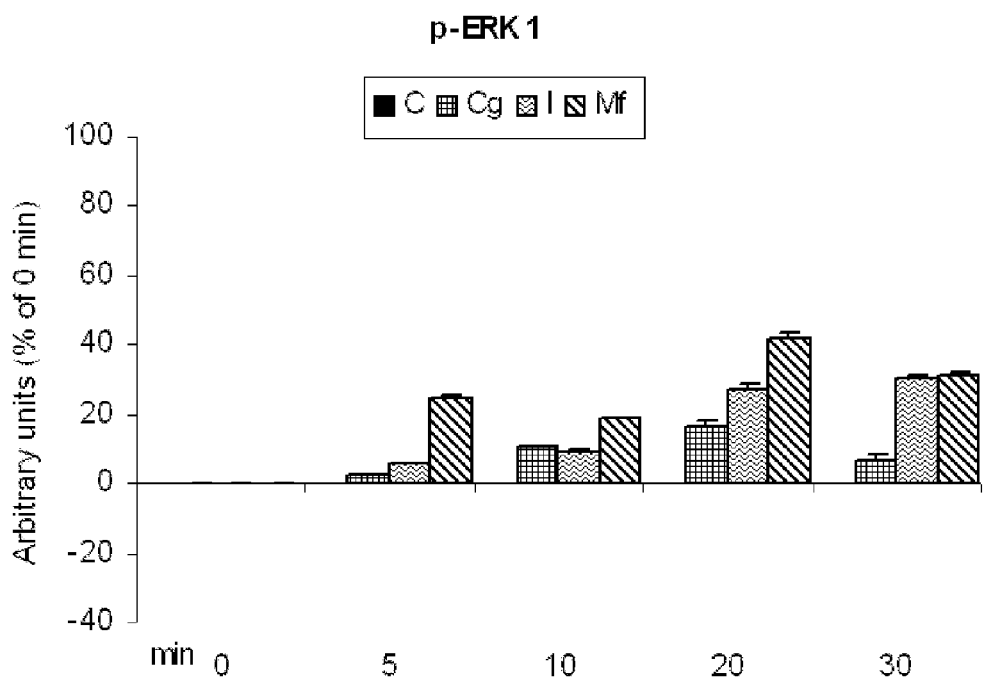

FIG. 14: Representative blot of ERK-1 phosphorylation in C2C12 myofibers when not stimulated (C) or after insulin (I), conglutin-γ (Cg) or metformin (Mf) stimulation at the times described in the Methods. The results of densitometry analyses are expressed as arbitrary units in relation to the amount of target protein at 0 min. Protein quantification was adjusted for the corresponding alpha-tubulin level.

Figure 15:
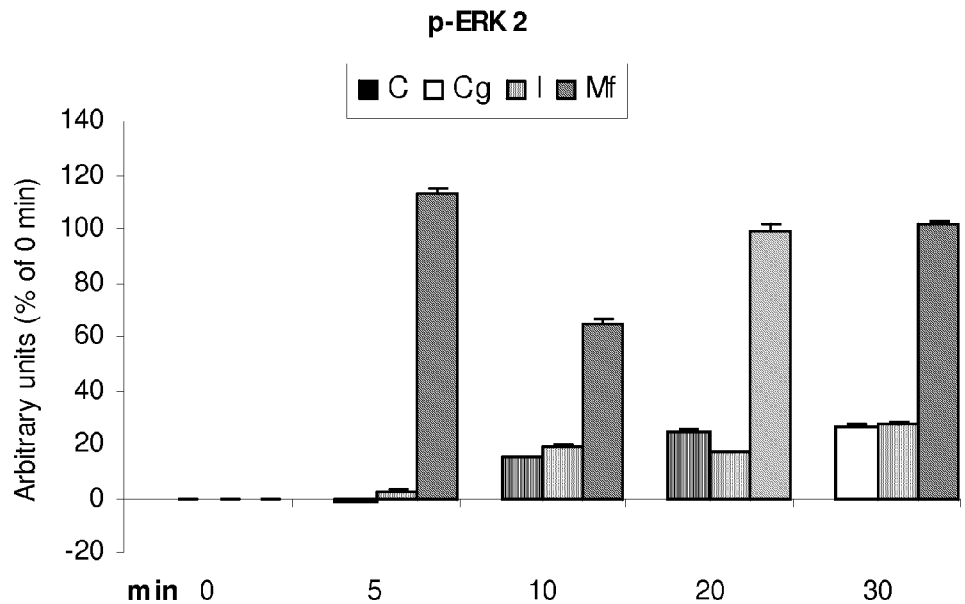

FIG. 15: Representative blot of ERK-2 phosphorylation in C2C12 myofibers when not stimulated (C) or after insulin (I), conglutin-γ (Cg) or metformin (Mf) stimulation at the times described in the Methods. The results of densitometry analyses are expressed as arbitrary units in relation to the amount of target protein at 0 min. Protein quantification was adjusted for the corresponding alpha-tubulin level.

Figure 16:
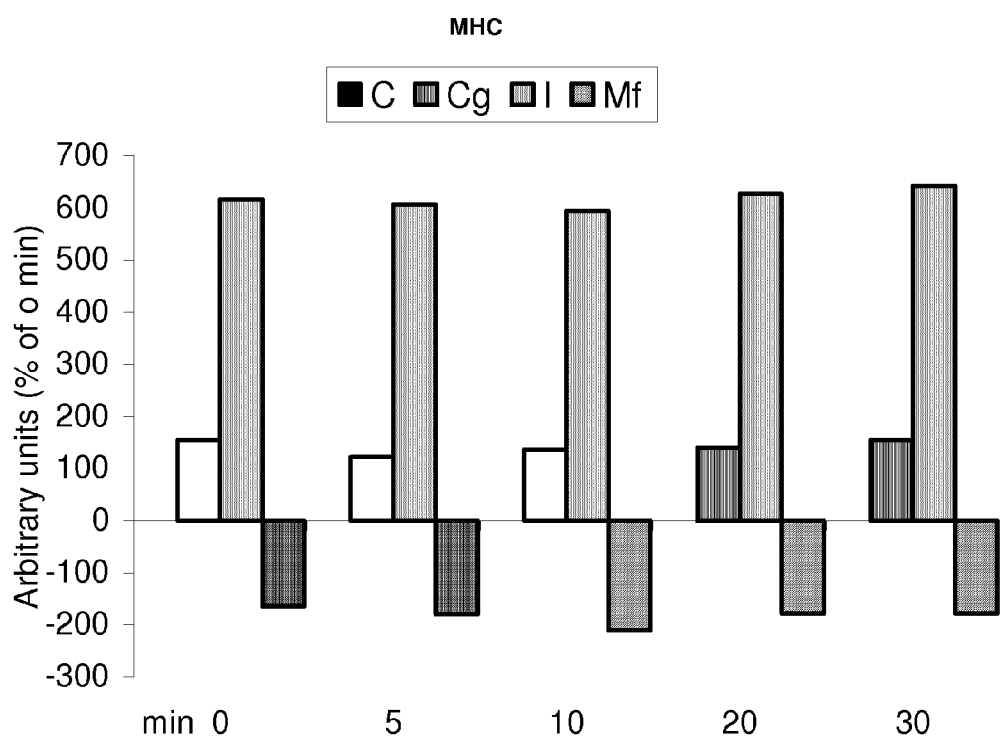

FIG. 16: Representative blot of MHC gene expression (protein content) in C2C12 myofibers when not stimulated (C) or after insulin (I), conglutin-γ (Cg) or metformin (Mf) stimulation at the times described in the Methods. The results of densitometry analyses are expressed as arbitrary units in relation to the amount of target protein at 0 min. Protein quantification was adjusted for the corresponding alpha-tubulin level.

Figure 17:
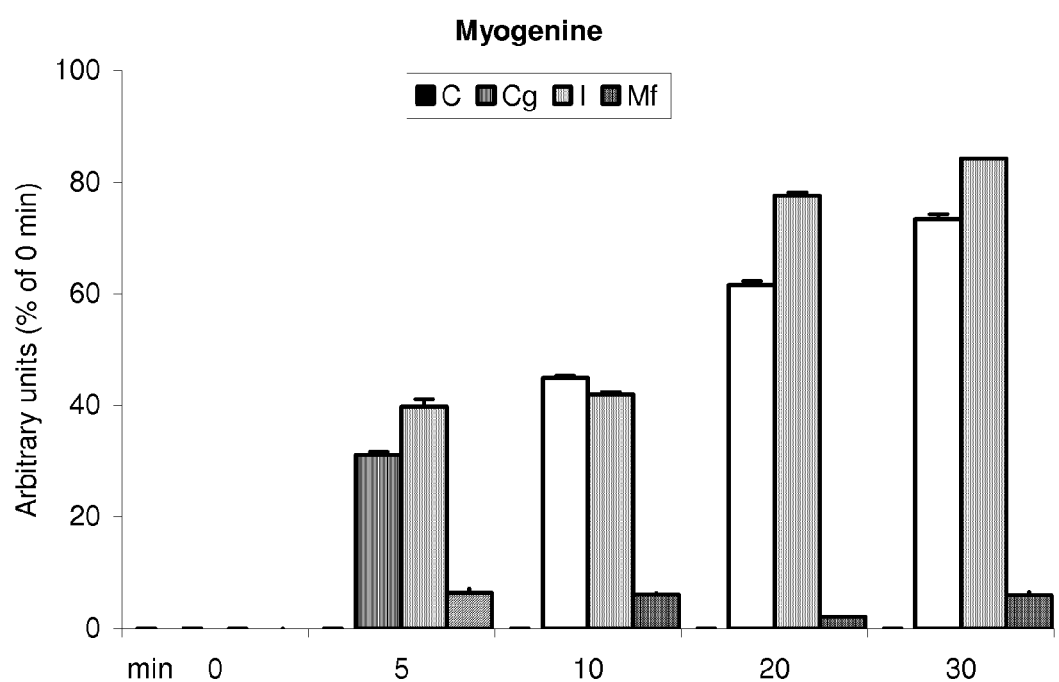

FIG. 17: Representative blot of myogenin content in C2C 12 myofibers when not stimulated (C) or after insulin (I), conglutin-γ (Cg) or metformin (Mf) stimulation at the times described in the Methods. The results of densitometry analyses are expressed as arbitrary units in relation to the amount of target protein at 0 min. Protein quantification was adjusted for the corresponding alpha-tubulin level.

Figure 18:
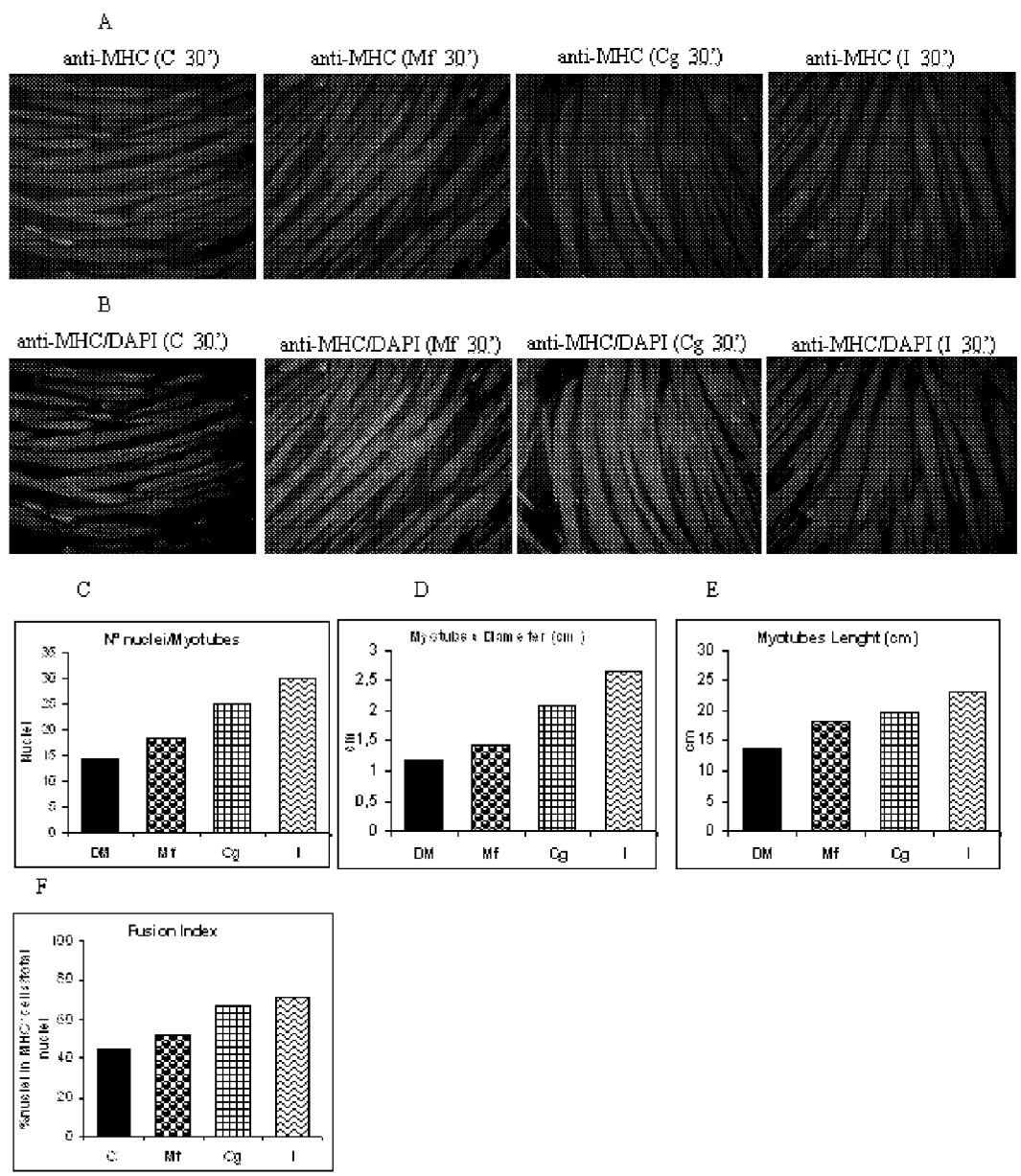

FIG. 18: C2C12 myoblasts were differentiated for 74 h and treated as described in the method section. A) MHC in myotubes of control and stimulated with Mf, Cg and I respectively, was detected by immunofluorescence (red). B) Images of MHC-positive myotubes were layed upon DAPI stained nuclei images. C) The nuclei present in MHC-positive myotubes were counted and the average graphically represented. D) The diameters of MHC-positive myotubes were measured and the average, expressed in cm, were graphically represented. E) The diameters of MHC-positive myotubes were measured and the average, expressed in cm, were graphically represented. F) The number of DAPI stained nuclei present in MHC-positive cells/number of total DAPI stained nuclei per microscopic field was determined and expressed as percentage.

Figure 19:
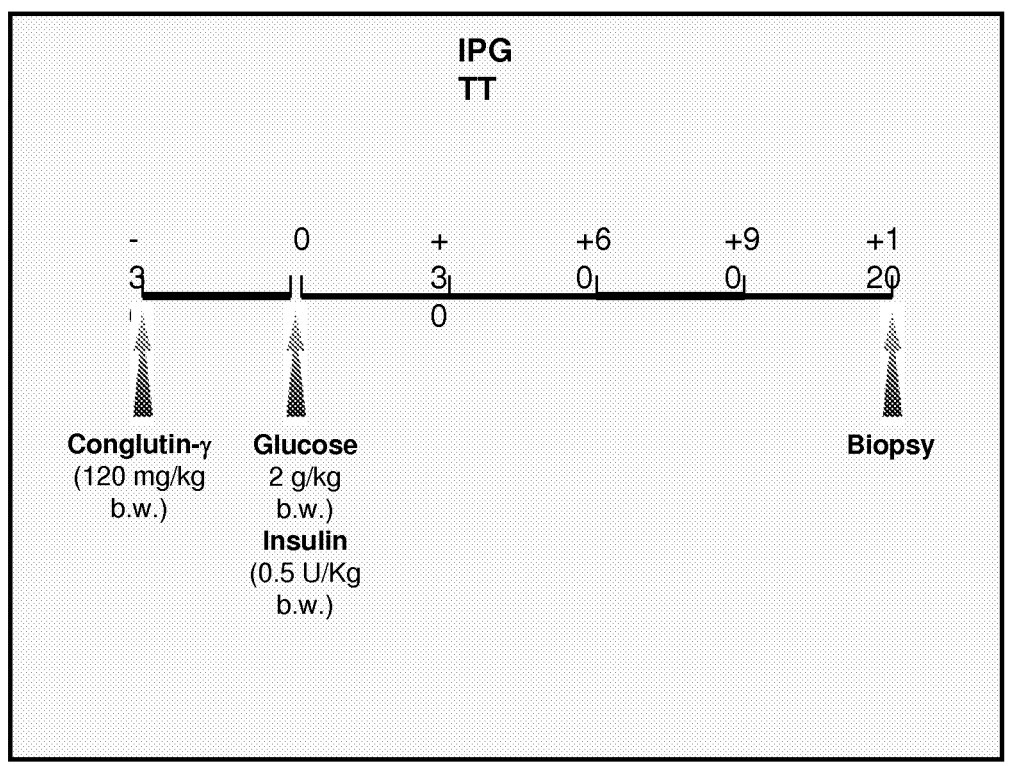

FIG. 19: Intraperitoneal glucose tolerance test (IPGTT) design (detailed description in the Methods section).

Figure 20:
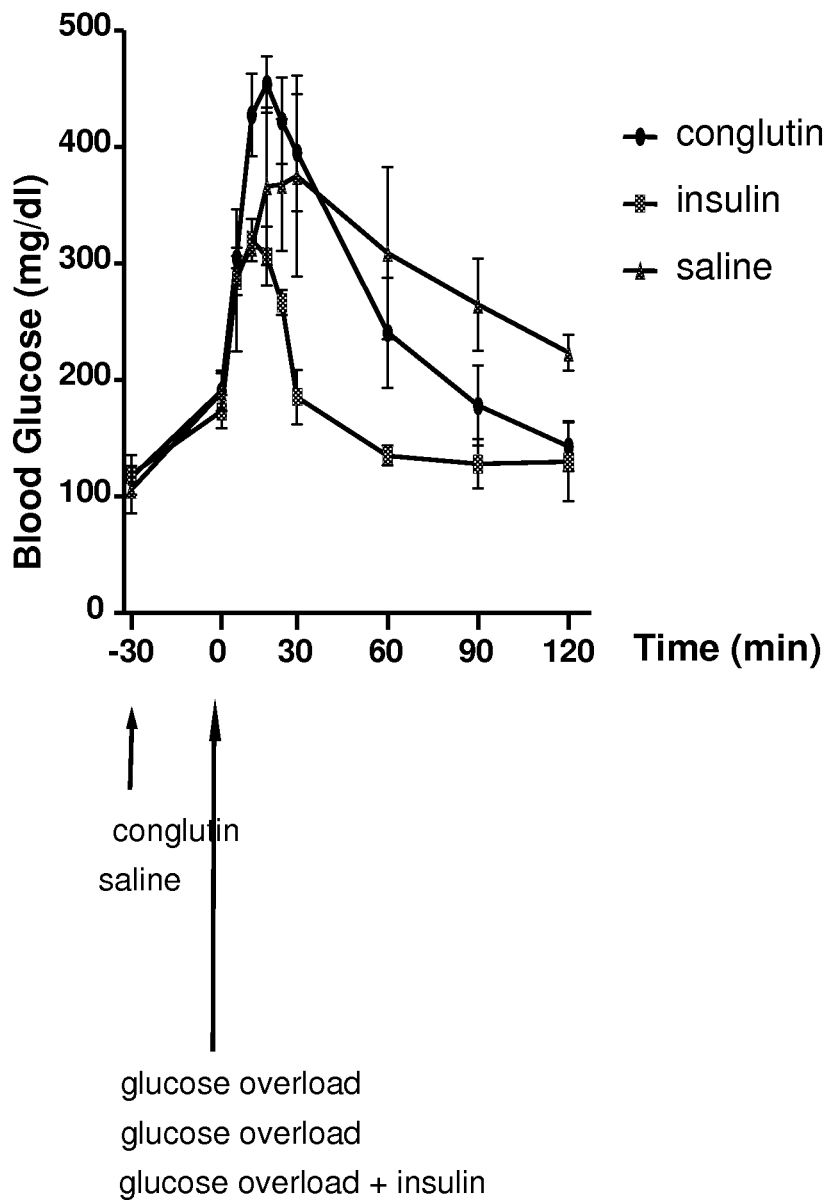

FIG. 20: Effect of conglutin-gamma and insulin treatment on IPGTT. The panel represents mean of blood glucose concentration during IPGTT registered for 3 mice in each group. Lines on symbols represent S.E.M.

Figure 21:
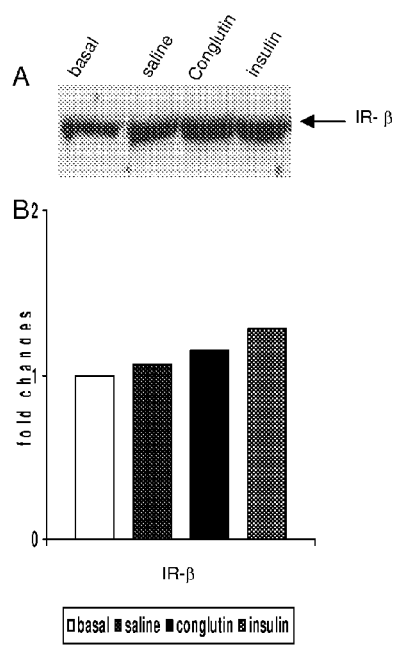

FIG. 21: Panel A: Representative blot of the insulin receptor beta (IR-beta) protein content in mice gastrocnemius muscle taken from the four groups of study at the end of the IPGTT (120 min)

Panel B: effect of insulin and conglutin-gamma on IR-beta protein expression in mouse gastrocnemius muscle collected at the end of the IPGGT study (120 min). Relative levels of protein expression were normalized to beta-actin. The fold change for each condition is calculated as the average expression over all treated samples divided by the average expression over all samples in basal condition.

Figure 22:
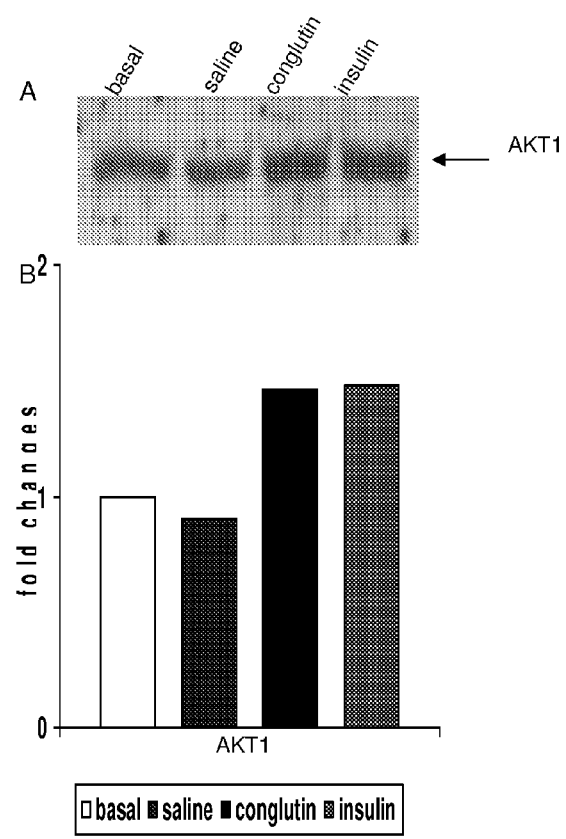

FIG. 22: Panel A: Representative blot of the AKT1 protein content in mice gastrocnemius muscle taken from the four groups of study at the end of the IPGTT (120 min).

Panel B: effect of insulin and conglutin-gamma on AKT1 protein expression in mouse gastrocnemius muscle collected at the end of the IPGGT study (120 min). Relative levels of protein expression were normalized to beta-actin. The fold change for each condition is calculated as the average expression over all treated samples divided by the average expression over all samples in basal condition.

Figure 23:
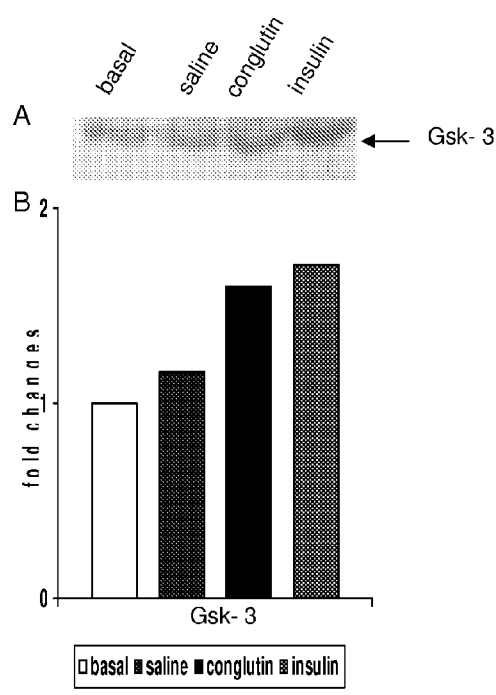

FIG. 23: Panel A: Representative blot of the GSK-3 protein content in mice gastrocnemius muscle taken from the four groups of study at the end of the IPGTT (120 min).

Panel B: effect of insulin and conglutin-gamma on GSK-3 protein expression in mouse gastrocnemius muscle collected at the end of the IPGGT study (120 min). Relative levels of protein expression were normalized to beta-actin. The fold change for each condition is calculated as the average expression over all treated samples divided by the average expression over all samples in basal condition.

Figure 24:
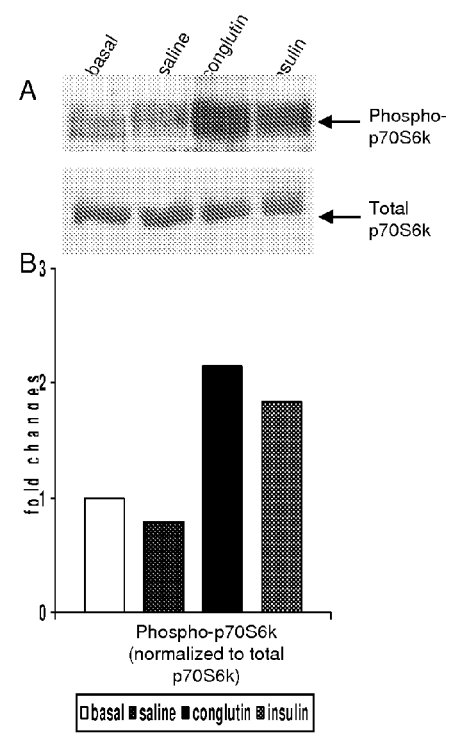

FIG. 24: Panel A: Representative blot of the p70S6k phosphorylation in mice gastrocnemius muscle taken from the four groups of study at the end of the IPGTT (120 min).

Panel B: effect of insulin and conglutin-gamma on p70S6k phosphorylation in mouse gastrocnemius muscle collected at the end of the IPGGT study (120 min). Values are ratios of phosphorylated to total p70S6k expression. Relative levels of protein expression were normalized to beta-actin. The fold change for each condition is calculated as the average expression over all treated samples divided by the average expression over all samples in basal condition.

Figure 25:
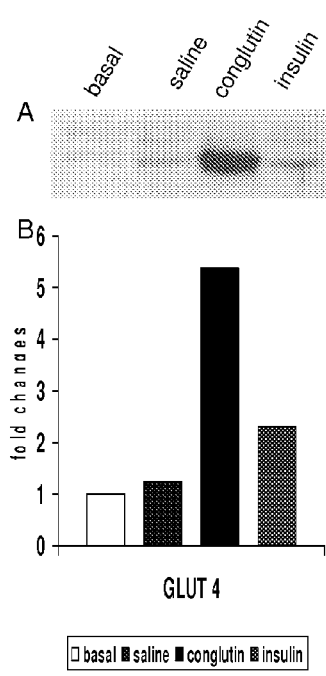

FIG. 25: Panel A: Representative blot of the Glut-4 protein content in mice gastrocnemius muscle taken from the four groups of study at the end of the IPGTT (120 min) Panel B: effect of insulin and conglutin-gamma on Glut-4 protein expression in mouse gastrocnemius muscle collected at the end of the IPGGT study (120 min) Relative levels of protein expression were normalized to beta-actin. The fold change for each condition is calculated as the average expression over all treated samples divided by the average expression over all samples in basal condition.

Figure 26:
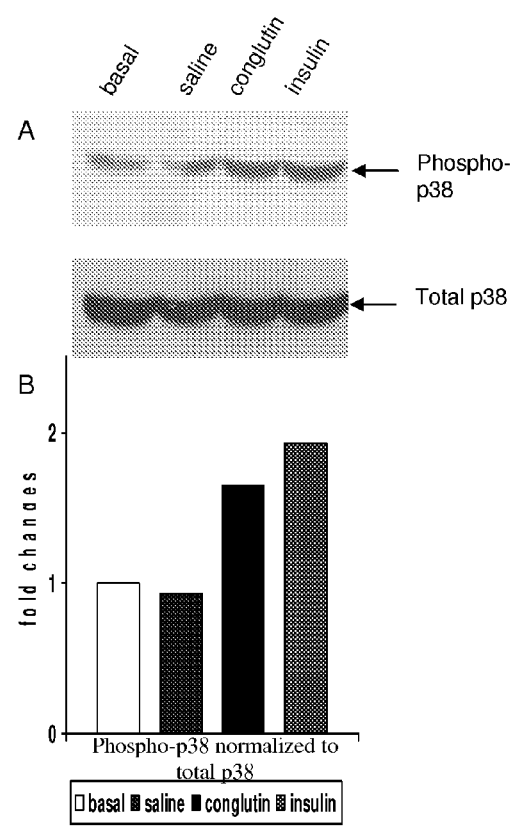

FIG. 26: Panel A: Representative blot of the p38 phosphorylation in mice gastrocnemius muscle taken from the four groups of study at the end of the IPGTT (120 min). Panel B: effect of insulin and conglutin-gamma on p38 phosphorylation in mouse gastrocnemius muscle collected at the end of the IPGGT study (120 min) Values are ratios of phosphorylated to total p38 expression. Relative levels of protein expression were normalized to beta-actin. The fold change for each condition is calculated as the average expression over all treated samples divided by the average expression over all samples in basal condition.

Figure 27:
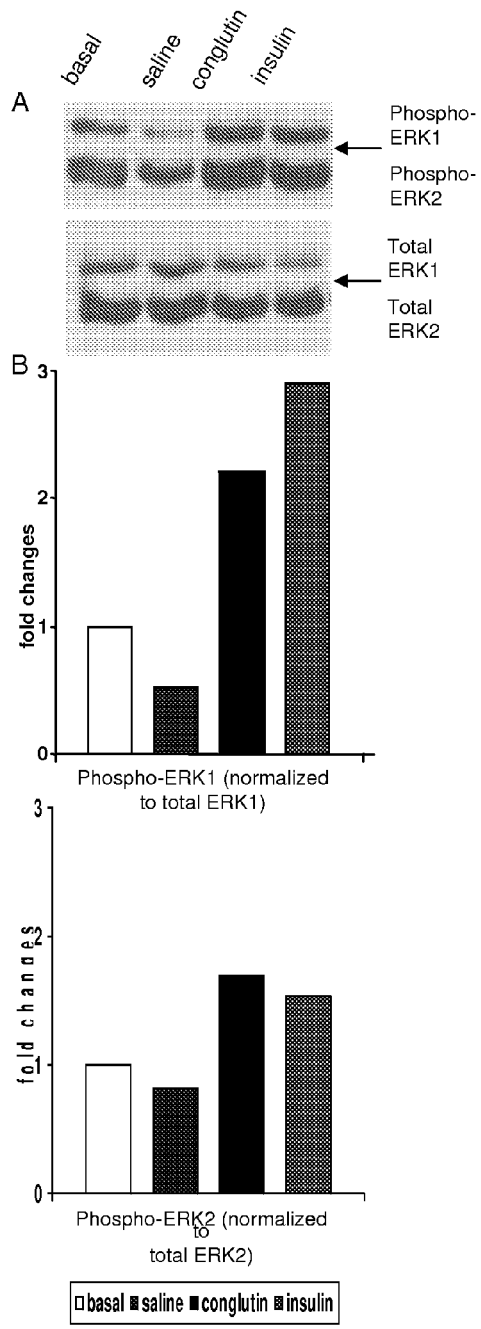

FIG. 27: Panel A: Representative blot of the ERK1 and ERK2 phosphorylation in mice gastrocnemius muscle taken from the four groups of study at the end of the IPGTT (120 min) Panel B: effect of insulin and conglutin-gamma on ERK1 and ERK2 phosphorylation in mouse gastrocnemius muscle collected at the end of the IPGGT study (120 min) Values are ratios of phosphorylated to total ERK1 and ERK2 expression. Relative levels of protein expression were normalized to beta-actin. The fold change for each condition is calculated as the average expression over all treated samples divided by the average expression over all samples in basal condition.

Figure 28:
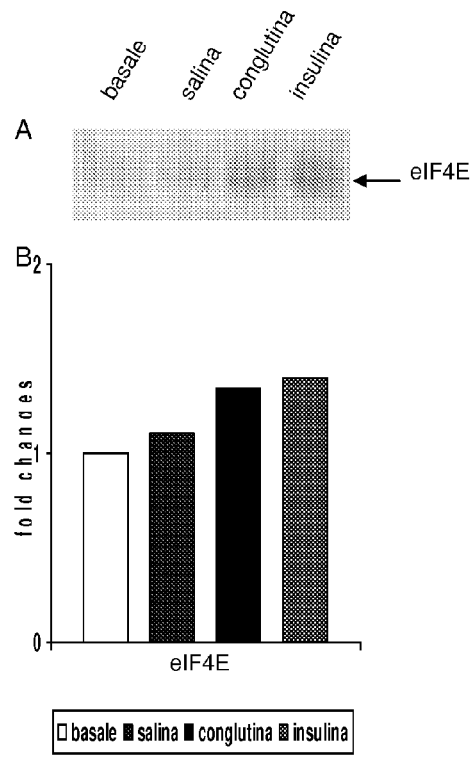

FIG. 28: Panel A: Representative blot of the eIF4E protein content in mice gastrocnemius muscle taken from the four groups of study at the end of the IPGTT (120 min) Panel B: effect of insulin and conglutin-gamma on eIF4E protein expression in mouse gastrocnemius muscle collected at the end of the IPGGT study (120 min) Relative levels of protein expression were normalized to beta-actin. The fold change for each condition is calculated as the average expression over all treated samples divided by the average expression over all samples in basal condition.

MATERIALS AND METHODS

Materials.

Anti-actin (I-19), anti-AKT (C-20), anti-caveolin-3 (A-3), anti-eIF4E (P-2), anti-flotillin-2 (H-90), anti-IRS1 (H-165), anti-myogenin, anti-P13-Kinase p85☐ (Z-8), anti-PKC (H-300), anti-beta-tubulin (TU-16), anti phopho-ERK (E-4), anti-MHC, anti-phospho-Cbl (Tyr700) and anti phosho-p70 S6 kinase (Thr421/Ser 424), anti-PHAS1, monoclonal or polyclonal primary antibodies and the peroxidase-conjugated secondary antibodies were purchased from Santa Cruz Biotechnology (Santa Cruz, Calif., U.S.A.). All other reagents were purchased from Sigma Chem. Co. (St. Louis, Mo., U.S.A.). Mouse C2C12 myoblastic cells were purchased from the European Collection of Animal Cell Cultures (ECACC).

Purification of Lupin Conglutin-γ.

Conglutin-γ was purified as described previously by using a combination of anion and cation exchange chromatography (1). The purified protein was freeze dried and resuspended in the appropriate buffers before use. For the estimation of conglutin-γ concentrations, optical measurements at 280 nm were made. The extinction coefficient of 1 for a solution of 1 mg/mL was used, according to (2).

Electrophoretic Techniques.

The SDS-PAGE was performed in NuPAGE Novex Bis-Tris 10% gels using a XCell SureLock Mini-Cell (Invitrogen, Milan, Italy). NuPAGE MES SDS Running Buffer and See-Blue Plus2 Prestained Standard (Invitrogen, Milan, Italy) were used. This procedure ensured the visualisation of polypeptides in the range of Mrs from 200 to 3 kDa. The gels were stained with SimplyBlue SafeStain (Invitrogen, Milan, Italy).

For protein blot analysis, the gel was transferred to nitrocellulose transfer membrane (Protran®, Whatman® Schleicher & Schuell) by blotting according to Towbin et al. (6) on a Trans-blot Electrophoretic Transfer Cell (Bio-Rad, Milan, Italy). The membrane was blocked with 3% gelatin for 2 hours and washed three times with 0.25% gelatin solution both in PBS buffer (10 mM NaPi, pH 7.4, containing 150 mM NaCl). Membrane was then soaked for 2 hours in PBS buffer containing rabbit anti-conglutin-γ in the ratio 1,500/1 (v/v). The antiserum was prepared and immuno-affinity purified as previously described. The bands were revealed by using horseradish peroxidase conjugate with goat-antirabbit antiserum 2,000/1 (v/v) (Bio-Rad, Milan, Italy) and hydrogen peroxide with 4-chloronaphtol as substrate.

Experimental Protocol.

C2C12 myoblasts were cultured at 37° C. in humidified 5% $CO_2$ atmosphere in a growth medium (GM) containing DMEM supplemented with 20% (v/v) FBS (fetal bovine serum), 1% penicillin-streptomycin and 1% L-glutamine. Cell differentiation was initiated by placing 70% confluent cell cultures in DMEM supplemented with 1% HS (horse serum) and antibiotics (DM). To prepare myotube cultures, myoblasts were cultured in DM for 72 hours. Cells used as control (C) were switched back to GM for the duration of the experiment. Other three groups of cells were replaced in GM with the selective addition respectively of insulin (I; 100 nM), conglutin-γ (Cg; 0.5 mg/ml) and metformin (Mf; 400 μM). For each experimental condition cells were lysed at 0, 5, 10, 20 and 30 minutes after the stimuli addition.

For immunofluorescence analysis C2C12 myoblasts differentiated as above were stimulated with insulin, conglutin-γ and metformin for 30 minutes. In differentiated cells immunostained with anti-MHC the DAPI stained nuclei per myotube, myotubes length and diameter were determined and expressed as average.

In Vivo Study.

For this protocol C57B1/6 wild type mice were utilized. Intraperitoneal glucose tolerance test (IPGTT) was performed by injecting glucose (2 g/kg body weight) i.p. in three groups of overnight-fasted mice. Thirty minutes before glucose administration, conglutin-gamma (120 mg/kg b.w.) was injected i.p. in the "Conglutin" group of mice. In the "Insulin" group of mice, insulin (0.5 U/kg b.w.) was administered i.p. at the same time of glucose injection (time 0). Blood glucose levels were determined prior (30 and 0 minutes) to injection and 30, 60, 90, and 120 min after injection. Blood samples were obtained from the tail vein and plasmas used to measure glucose concentration by the glucose reflectometer. At the end of the study gastrocnemius muscle was taken. A group of overnight-fasted mice (basal) was sacrificed before the study and gastrocnemius muscle taken. A group of animals that received saline instead of insulin or conglutin-gamma, was used as control (saline).

Immunoblotting Analysis.

C2C12 myofibers were homogenized in lysis buffer (50 mM Tris/HCl, pH 7.4, 150 mM NaCl, 1% Triton X-100, 1 mM sodium orthovanadate ($Na_3VO_4$), 1 mM EDTA, 1 mM PMSF, 1 mg/ml aprotinin, 1 mg/ml leupeptin, 1 mg/ml pepstatin) and shaked for 1 h at 4° C. Detergent-insoluble material was removed from the cell suspension by centrifugation at 12,000×g for 30 min. Aliquots of 30 ☐g supernatant proteins from the different samples were resolved by 8% (IRS1, MHC, myogenin and p-CBL), 10% (PI3K p85, AKT1, p-p70 S6K and PKC), 12% (eIF-4E, p-ERK1, p-ERK2, caveolin-3 and flottilin-2) and 15% (PHAS1) SDS-PAGE (Sodium Dodecyl Sulfate—PolyAcrylamide Gel Electrophoresis). Electrophoresed proteins were transferred onto nitrocellulose membranes using a Bio-Rad Mini Trans-Blot system. The blots were blocked with 50 mg/ml non-fat dry milk in 20 mM Tris/HCl, pH 7.4, 100 mM NaCl for 1 h at room temperature and then incubated overnight at 4° C. with respective primary antibodies in 10 mg/ml non-fat dry milk, 20 mM TRIS/HCl pH 7.4 and 100 mM NaCl and 0.3% Tween 20. After several washes the membranes were incubated with species-specific secondary antibodies. Immunoreactive bands were visualized by an enhanced chemiluminescence method (Amersham Pharmacia Biotech, Piscataway, N.J., USA).

The membrane was stripped and re-probed with an antibody to actin or tubulin to confirm equal protein loading per sample. Quantitative measurement of immunoreactive bands was performed by densitometric analysis using the Scion image software (Scion corporation, Frederick, Md., USA).

Muscle Biopsies Immunoblotting Analysis.

Collected gastrocnemius muscle was frozen in liquid nitrogen immediately after excision and then stored at –80° C. A gram of tissue with 1.5 ml of ice cold RIPA buffer was disrupted and homogenized with a dounce homogenizer, maintaining temperature at 4° C. throughout all procedures, then incubated on ice for 30 minutes. The homogenate was transferred to microcentrifuge tubes, centrifugated at 10,000×g for 10 minutes at 4° C. The supernatant fluid containing the mice skeletal muscle tissue total protein was subjected to SDS-PAGE and immunoblotting using enhanced chemiluminescence (ECL) detection as described in the "immunoblotting analysis" of the Methods section.

Immunofluorescence Analysis.

For immunofluorescence, cells were fixed in 4% paraformaldehyde, permeabilized with 0.2% Triton X-100, and blocked with PBS containing 1% bovin serum albumin. Cells were then immunostained with anti-MHC rhodamine conjugated and nuclei revealed with DAPI staining.

Results

Homogeneity of Lupin Conglutin-γ.

FIG. 2A shows the SDS-PAGE pattern under reducing conditions of the purified conglutin-γ as compared to the total lupin protein extract. Two main bands of Mr around 30 and 16-17 kDa were visible. The sizes of these bands fitted with those of the large and small conglutin-γ subunits. A minor band of 48 kDa was previously found to correspond to uncleaved conglutin-γ precursor. This protein preparation was judged sufficiently homogeneous to be suitable for cell trials. The protein blot with specific antibodies (FIG. 2B) confirmed the identity of the proteins and the lack of apparent differences between the purified conglutin-γ and the one in the total protein extract suggesting that no modification had occurred during the purification procedure.

Analyses of Insulin Signaling Protein.

In their previous works, the authors of the present invention focused their investigation on the insulin-modulated pathways involved in protein anabolism, glucose homeostasis, gene expression and mRNA translation regulation, in different tissues. (7-9). To evaluate the insulin-mimetic effect of conglutin-γ, they observed the ability of both insulin and lupin protein to stimulate the same pathways in vitro. Metformin, the first-line oral anti-diabetic drug of choice for the treatment of type II diabetes, was used as a positive control. FIG. 3 illustrates typical patterns of IRS-1 observed on western blots of C2C12 myotube at different time of stimulus by insulin, conglutin-γ or metformin (time course). Insulin maximally stimulated the IRS-1 protein content within 20 minutes by ~32%, but protein stimulation was higher (~35%) at 10 minutes when stimulated by conglutin-γ. Metformin exerted a gradual increment of IRS-1 activation, which was maximal at 30 minutes (~76%).

Insulin enhanced p85-PI3 kinase activation (FIG. 4) within 5 minutes (~62%) and the effect was persistent up to the end of the experiment (~56%). The effect of conglutin-γ was slower but robust, with a peak effect at 30 minutes (~40%). FIG. 5 shows the activation of Akt-1, a downstream target of PI 3-kinase involved in insulin-signaling pathway leading to glucose utilization, glycogen and protein synthesis, and CAP dependent translation. Insulin and conglutin-γ modified the concentration of Akt-1 protein at 20 minutes (~13% and 33%, respectively), while metformin exerted its maximal effect at 5 minutes (~20%).

To explore the pathway involved in protein synthesis, the authors investigated whether insulin and conglutin-γ were able to induce the phosphorylation of p70S6K, PHAS-1 and eIF-4E in C2C12 myotube. As seen in FIG. 6, insulin induced a p70S6K phosphorylation within 5 minutes (~40%) up to 30 minutes (~94%). Conglutin-γ exerted a maximum stimulus on p70 S6 kinase phosphorylation within 5 minutes (67%) which persisted but gradually decreased until 30 minutes (~50%). Metformin exerted a maximal effect on p70S6K phosphorylation within 10 minutes (~46%) that decreased until 30 minutes (~32%).

PHAS-1 appears on the blot as a rapidly migrating band arbitrarily designated α (PHAS-1A) and a more slowly migrating band β (PHAS-1B) representing the more active form of the enzyme. Figures (FIGS. 7 and 8) show that the density of α and β bands are more increased in conglutin-γ, insulin and metformin stimulated cells in respect to the control.

FIG. 9 represents the amount of eIF4E after insulin or conglutin-γ stimulation in C2C12 myotube. Insulin enhanced eIF4E protein concentration with a persistent effect from 5 to 20 minutes (~45%). This effect decreased but persisted until the end of the experiment (~30%). Conglutin-γ stimulated eIF4E protein concentration in 5 minutes (~21%). and the effect increased up to 30 minutes (~68%). Metformin was not able to exert an activation of eIF4E enzyme. Glucose transporter of muscle and adipose cells is regulated by insulin through post-translational events. PKC, a downstream kinase of insulin receptor and phosphatidylinositol (PI) 3-kinase, plays a very important role in activating glucose transport response, but this pathway is not sufficient to produce GLUT4 translocation. A separate PI3K-independent pathway, involving the insulin-stimulated tyrosine phosphorylation of CBL, promotes the GLUT4 translocation to the plasma membrane. Expression of flottilin-2 and caveolin-3 is necessary for the activation and the modulation of this pathway. The authors studied the activation of the proteins involved in these pathways, by insulin and conglutin-γ. Conglutin-γ increased the PKC concentration (FIG. 10) at the same values at 10 (~28%) and 20 minutes (~26%), which decreased to ~20% at the end of the experiment. Insulin effect was earlier (5 minutes) and maximum at 20 minutes (~32%). Metformin was able to stimulate protein concentration more than the other two stimuli. Also flottilin-2 protein concentration, increased from 5 to 30 minutes in all the tested conditions, as represented in FIG. 11, with a peak at 10 minutes by insulin (~60%) and conglutin-γ(~52%). Metformin did not exert any flottilin-2 activation. Caveolin-3 protein concentration was increased by both conglutin-γ and insulin with a maximum stimulus at 10 minutes (~22%) and 30 minutes (~34%) respectively, as represented in FIG. 12. Metformin exerted an higher stimulation with respect to the other stimuli, which was up and above 70% toward the end of the experiment. The data presented in FIG. 13 show conglutin-γ and insulin ability to maximally phosphorylate Cbl at 10 minutes (~64%) and 30 minutes (~56%) respectively. ERKs were also investigated as candidate kinases necessary for the stimulation of gene transcription and glycogen synthesis by insulin. The authors used their experimental model to clarify the possible implication of conglutin-γ on modulation of ERK1 and ERK2 activity. Both insulin and conglutin-γ were able to modify ERK1 and ERK2 concentration respect to the control group, as showed in FIG. 14 and FIG. 15. Conglutin-γ increased gradually ERK2 activation to a maximum (~27%) at 30 minutes, while ERK1 activation reached a peak at 20 minutes (~17%) followed by a decrease. Insulin caused a maximal activation of ERK1 at 20 minutes (~27%) that persisted up to the end of the experiment. Regarding in ERK2 insulin stimulation was earlier (10 minutes ~20%) and reached a peak at 30 minutes (~28%). Metformin exerted a higher activation in both ERK1 and ERK2 with respect to the two other stimuli.

Insulin, after binding to its receptor, regulates the expression of several genes (10). To evaluate if conglutin-γ is able to exert a gene transcription control through ERK1/2 pathway, the authors studied MHC muscle-specific gene expression, whose activity is responsible for a tissue differentiation process. As shown in FIG. 16, conglutin-γ (as insulin) was surprisingly able to increase MHC expression (~155% and ~600% respectively) with respect to the un-stimulated differentiated muscle cells, but metformin was not able to induce the same gene expression.

Moreover the authors studied the expression of myogenin, a transcription factors that plays a pivotal role in the activation of muscle-specific gene MHC. FIG. 17 shows that myogenin activation by insulin and conglutin-γ was overlapping. Also in this case metformin did not exert any effect.

To validate the effect of the stimuli on MHC expression and myoblasts differentiation as well as to investigate whether such stimuli implement the recruitment of myoblasts into myotubes, or myotubes hypertrophy, differentiated C2C12 cells were stimulated with conglutin-γ, insulin and metformin for 30 minutes and 2 h respectively. It was observed that three-day differentiated myoblasts formed hypernucleated myotubes with increased cell size. Images of MHC-positive myotubes detected by immunofluorescence (FIG. 18 A) layed upon DAPI stained nuclei (FIG. 18 B) showed that the number of nuclei present in MHC positive myotubes (FIG. 18 C), myotubes diameter (FIG. 18 D) and length (FIG. 18 E) and fusion index gradually increase in cells stimulated with Mf, Cg or I compared with the un-stimulated differentiated muscle cells.

These studies were prompted by the knowledge that lupin seeds are referred to as an antidiabetic drug in the traditional medicine. Since the first finding at the beginning of the '30s (11, 12), various authors have attempted the isolation of lupin components with glycemic lowering properties. Among lupin components, lupin alkaloids and other soluble fractions were identified. Our recent publication indicates that in conglutin-γ is the active compound which lowers blood glucose (4).

The authors presently investigate the effect of conglutin-γ in the activation of the next different intracellular kinase pathways:
1) IRS-1/PI-3-kinase. Incubation of cells with conglutin-γ causes the activation of the intracellular pathway eventually involved in GLUT-4 translocation and glucose transport (5). Specifically conglutin-γ causes a 30% activation of IRS-1 with a peak at 20 minutes (FIG. 3). Insulin also peaks at 30 minutes in the activation of IRS-1 (~35% increase above basal). A similar pattern was shown for the phosphorylation of PI-3-kinase p85 subunit (FIG. 4) with the difference of a later peak (30 minutes) for both insulin and conglutin.

2) p70 S6 kinase/eIF-4E. The phosphorylation of p70 S6 kinase and eIF-4E has been associated to the stimulation of protein synthesis. The eukaryotic translation initiation factor eIF4E released as a result of PHAS-1 phosphorylation, acts in the rate-limiting step of translation initiation and promotes the messenger RNA (mRNA) export of several genes involved in the cell cycle and growth (13). The present data show that incubation of mouse myoblasts with conglutin-γ stimulates p70 S6 kinase and eIF-4E activation as shown in FIGS. 6 and 9. Moreover, conglutin-γ is able to stimulate PHAS-1 activation (FIGS. 7, 8). Phosphorylation of AKT-1 is upstream the phosphorylation of p70 S6 kinase as well as of eIF-4E activation, and insulin and conglutin-γ show comparable effects on its phosphorylation with a modest stimulation above basal at any time (FIG. 5);

3) Erk-1/Erk-2. Both conglutin-γ and insulin show a robust activation of pathways of endocellular kinases correlated with mitogenic activity of the cell and nuclear signaling. Both Erk-1 and Erk-2 are activated by conglutin-γ up to a peak stimulation of ~35% at 20 min, whilst insulin reaches a maximal activation at 30 minutes (FIGS. 14, 15).

4) Flottilin-2/caveolin-3 GLUT4. Recruitment from intracellular stores to the plasma membrane is a critical step for glucose uptake after insulin stimulation. In skeletal muscle cells Flotillin-2 and caveolin-3 coordinately modulate the insulin-stimulated translocation of GLUT4, localized to perinuclear domains containing flotillin-2, to selective domains of sarcolemma. Upon insulin stimulation, caveolae microdomains containing caveolin-3 and the insulin receptor, move away from the plasma membrane toward the cytoplasm and temporarily interact with flotillin-2/GLUT4-containing domains before they reach the sarcolemma. The insulin receptor moves from caveolin-3-containing domains to flotillin-1-containing domains, on whose surface is GLUT4. Happened switching, GLUT4, together with flotillin-2, moves to the sarcolemma, promoted by the insulin-stimulated tyrosine phosphorylation of CBL (14). The present results show that conglutin-γ increases both flottilin-2 and caveolin-3 concentration (FIGS. 11 and 12) and CBL phosphorylation (FIG. 13), playing an important role in the vesicular transport of GLUT4 and in the regulation of muscle energy metabolism, through the modulation of key components of the insulin signalling.

The robust insulin-like activity of conglutin-γ is surprising since its tertiary structure is neither similar to the one of insulin, nor to the one of any insulin-mimetic known compound. Nonetheless, conglutin-γ shares with insulin some physical-chemical features: 1) in vitro, conglutin-γ binds with an high affinity to insulin itself. This may partially explain the striking insulin-like activity shown in this study; 2) like insulin, conglutin-γ is capable of binding metal ions including $Zn^{++}$, $Cu^{++}$, $Cd^{++}$, $Co^{++}$ in a decreasing order of affinity (15). The relevance of this metal ion binding capacity concerning the biological action of conglutin-γ is still to be evaluated. In contrast, at striking difference with insulin, conglutin-γ is highly resistant to gastric enzymes digestion, maintaining its activity after absorption, although studies of pharmaco-kinetics of conglutin-γ are still lacking. This last property makes obviously this natural protein highly appealing as a treatment for not only type 2 but also type 1 diabetes.

Beyond the already shown properties as a plasma glucose lowering agent (4), the discovery of this novel mechanism of action makes conglutin-γ suitable as an insulin-sensitizing compound, both as a drug or a food integrator in obesity and many other insulin-resistant conditions like metabolic syndrome (16), policistic ovary (17) and HIV-lipodystrophy (18).

Conglutin-γ is not the only plant protein which retains insulin-binding properties. In two papers of the '90s, a Japanese group showed an unusual insulin-binding activity of a soybean protein, named basic globulin 7S (Bg7S) (19, 20). However, no further studies on the effects of this protein on blood glucose level were carried out. Interestingly, in the course of the author's purification and characterization work on lupin seed proteins, which dates back to the middle of the '70s, the authors identified a lupin protein, other than conglutin-γ, that was later found to have 64% amino acid sequence identity with soybean Bg7S. The lupin seed hypoglycemic effects and the presence of a Bg7S-related protein in lupin makes it reasonable to speculate on the existence of a family of plant proteins, which share physical-chemical properties with mammalian insulin.

While insulin has been known to modulate intracellular metabolism by regulating the activity of several intracellular signaling pathway for a long time, in the recent years there have been considerable advances in the understanding of mechanisms by which insulin regulates gene transcription. Insulin has been shown to regulate, both in a positive and negative manner, the expression of hundreds of genes encoding proteins involved in a wide variety of biological activities. In particular, studying the impact of hyperinsulinemia on myosin heavy chain (MHC) gene regulation in human skeletal muscle (21), it was shown that insulin exerts a rapid influence at the transcriptional level for the MHC protein, indicating that insulin may contribute to the regulation of MHC gene expression. In the present invention, the authors find that insulin is able to increase more than six hundred times MHC gene expression with respect to the control group. In addition, the expression of MHC gene results positively regulated by conglutin-γ in respect of the un-stimulated differentiated muscle cells. Overall, the present results demonstrate that MHC genes expressed in muscle tissues is transcriptionally regulated by both insulin and conglutin-γ, while metformin is unable to produce the same effect.

The expression of muscle-specific genes that control the progress of muscle cells differentiation is regulated by a number of muscle-specific proteins. In particular, myogenin, a transcription factors of the basic helix-loop-helix type, plays a pivotal role in the activation of muscle-specific gene MHC and is critical for skeletal muscle development. Myogenin is absent in undifferentiated cells and is overexpressed in myoblasts committed to myogenic fate and in muscle terminal differentiation. In the present application, the authors provided evidences that both conglutin-γ and insulin, was able to enhance mouse C2C12 myoblastic cells differentiation as shown by an increase in the accumulation of differentiation markers such as MHC and myosin. Moreover, the present data indicate that conglutin-γ, such as insulin, allows the recruitment of myoblasts, enhancing their fusion into multi-nucleated myotubes and promoting increment of their length and diameter. The present data provide evidence that conglutin-γ and insulin influence muscle cells differentiation and contribute to the regulation of muscle growth. Then conglutin-γ or functional derivatives thereof can be used as diet integrators and food additive.

Insulin helps the body to use glucose for energy. The glucose tolerance test (FIG. 19) as used to study the ability of conglutin-gamma to help glucose enter the cells in mice. During the IPGTT (FIG. 20), there was an increment in plasma glucose levels in the three groups of study immediately after glucose administration, although "conglutin" mice had higher glucose levels. Blood glucose concentration decreased rapidly after insulin and more slowly after conglutin administration, but in both conditions at the end of the study (120 min) it returned to the same basal value concentration (~120 mg/dl). Thus conglutin-gamma appears capable of facilitating the entry of glucose in the muscle of mice mimicking the effect of insulin. To evaluate if conglutin-gamma uses the same insulin receptor to act on this pathway, we studied the effect of the lupin seed protein on IR-beta. The histograms in FIG. 21 shows a trend towards IR-beta protein content increment in the muscle of mouse treated with conglutin-gamma and insulin with respect to the basal and saline group. This data might indicate that insulin and conglutin-gamma perform their action at the cellular level by activating a common receptor.

Skeletal muscle represents a tissue that is responsive to Akt, whose action has been linked to skeletal muscle development, regeneration, and hypertrophy through several pathways that culminate in stimulation of protein synthesis, inhibition of atrophy, and prevention of cell death.

It was found through selective gene knockdown that Akt1 is necessary for initiation and maintenance of myoblast differentiation and loss of Akt1 inhibits activity of the myogenic transcription factor MyoD, showing that Akt1 promotes and sustains muscle differentiation.

Authors evaluated AKT1 expression in mice muscle and FIG. 22 (panel B) shows that conglutin-gamma, as well as insulin, was able to increase AKT1 expression with respect to the untreated muscle.

Cleasby et al. (22) have found that AKT overexpression results in significant human muscle hypertrophy, consistent with increment in p70S6kinase phosphorylation and glycogen accumulation. In particular Akt-1 increases glycogen synthase kinase-3 (GSK3) phosphorylation.

Authors undertook western analysis of gastrocnemius muscle lysates to determine the phosphorylation status of key signalling molecules downstream of Akt. Data show that glycogen synthase kinase GSK-3 and p70S6k phosphorylation was increased by both conglutin-gamma and insulin, as shown in FIGS. 23 and 24 respectively.

Glut4 is a protein that functions as an insulin-regulated facilitative glucose transporter. In the absence of insulin, this integral membrane protein is sequestered within the cells of muscle and adipose tissue. Within minutes of insulin stimulation, the protein moves to the cell surface and begins to transport glucose across the cell membrane.

Exercise also induces an increase in the GLUT4 isoform of the glucose: the GLUT4 protein is recruited from intracellular and moves to the cell surface, where it mediates the transport of glucose into the muscle cells. It was shown the ability of an acute bout of exercise to enhance skeletal muscle glucose uptake in vivo in humans. This adaptive increase in GLUT4 transporter makes possible more rapid glycogen storage after glycogen depleting exercise.

Besides, exercise was shown to result in activation of p38 MAPK which phosphorylates and activates PGC-1α in the cytosol. The activated PGC-1α moves into the nucleus and co-activates the transcription factors that regulate expression of mitochondrial proteins, thus inducing increase in mitochondrial biogenesis.

The study in mice muscle confirms the above mentioned effect of insulin and shows, moreover, the ability of conglutin-gamma to mimic these effects by facilitating the endocellular glycogen storage through the glut4 activation and p38 MAPK phosphorylation, as shown in FIGS. 25 and 26 respectively.

Previous studies in rat skeletal muscle have established that physical exercise, a physiological stressor, and insulin, a metabolic stimulator and growth factor, modulate the c-jun NH2-terminus kinase (JNK), and the extracellular regulatory kinases (ERK1 and ERK2) signaling pathways.

In particular, working with rat ventricular cardiomyocytes, Gillespie-Brown et al. (23) showed that constitutively active MEK1 stimulates the expression of genes characteristic of hypertrophy. Although the mechanism of the involvement of ERK signaling in skeletal muscle hypertrophy remains unknown, Shi et al., (24) speculate that it may work through protein accretion by mediating the phosphorylation of eukaryotic initiation factor eIF4E.

In the present study, authors evaluated ERK1/2 and eIF4E activation and, as shown in FIGS. 27 and 28, both insulin and conglutin are able to increment ERKs phosphorylation and eIF4E activation.

The data suggest that conglutin-gamma increased mitochondrial biogenesis and glucose intake in skeletal muscle thus improving endurance performance

REFERENCES

1. Duranti M, et al., Eur J. Biochem. 1994 Jun. 1; 222(2):387-93.
2. Duranti M, et al., J Agric Food Chem. 2000 April; 48(4):1118-23.
3. Duranti M, et al., Eur. J. Biochem. 1995; 230(3):886-91.
4. Magni C et al., J Nutr Biochem. 2004 November; 15(11):646-50.
5. Saltiel A R, Kahn C R. Nature 414:799-806, 2001.
6. Towbin H, et al., Proc Natl Acad Sci USA. 1979 September; 76(9):4350-4
7. Terruzzi I, et al., Mol Cell Endocrinol. 2002; 190:135-45.
8. Pellegatta F, et al., J Cardiovasc Pharmacol. 2006; 47:643-9.
9. Terruzzi I, Pellegatta F, Luzi L. Acta Diabetol. 2005; 42:139-46
10. Culjkovic B, et al., J Cell Biol. 2006; 175:415-26.
11. A. Ferranini and M. Pirolli, Folia Medica 23 (1937), pp. 729-748.
12. G. Orestano, Arch Farmacol. Sperim. 70 (1940), pp. 113-117)
13. Mounier C, Posner B I. Can J Physiol Pharmacol. 2006 July; 84(7):713-24.
14. Fecchi K, et al., FASEB J. 2006, 20(6):705-7.
15. Duranti M, et al., Phytochemistry. 2001 March; 56(6):529-33
16. Grundy S M. J Clin Endocrinol Metab. 2007; 92:399-404.
17. Santana L F, et al., Gynecol Endocrinol. 2004 August; 19(2):88-96.
18. Luzi L, et al., Am J Physiol Endocrinol Metab. 2003 February; 284(2):E274-80.
19. Komatsu S, Hirano H. FEBS Lett. 1991 Dec. 9; 294(3):210-2.
20. Watanabe Y, et al., Eur J. Biochem. 1994 Aug. 15; 224(1):167-72.
21. Houmard J A, et al., J Appl Physiol. 1999 June; 86(6):1828-32.
22. Cleasby M E, et al., Mol Endocrinol. 2007 January; 21(1):215-28.
23. Gillespie-Brown, et al., J Biol Chem. 1995 Nov. 24; 270(47):28092-6.
24. Li X, et al., Chin Med J (Engl). 2002 May; 115(5):658-63
25. Sirtori, C. R., et al., J. Nutr. 2004 January; 134(1):18-23

The invention claimed is:

1. A method to induce muscle cell differentiation or muscle growth comprising:
    obtaining an enriched conglutin-γ protein extract from lupin seeds comprising between 10 and 30% by weight of conglutin-γ; and
    exposing muscle cell or muscle to an effective amount of the enriched conglutin-γ protein extract thereby inducing muscle differentiation or muscle growth.

* * * * *

UNITED STATES PATENT AND TRADEMARK OFFICE
CERTIFICATE OF CORRECTION

PATENT NO. : 8,609,161 B2  Page 1 of 1
APPLICATION NO. : 12/994959
DATED : December 17, 2013
INVENTOR(S) : Luzi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 207 days.

Signed and Sealed this
Twenty-second Day of September, 2015

Michelle K. Lee
*Director of the United States Patent and Trademark Office*